(12) United States Patent
Nautiyal et al.

(10) Patent No.: US 7,097,830 B2
(45) Date of Patent: Aug. 29, 2006

(54) SYNERGISTIC BIOINOCULANT COMPOSITION COMPRISING BACTERIAL STRAINS OF ACCESSION NOS. NRRL B-30486, NRRL B-30487, AND NRRL B-30488 AND A METHOD OF PRODUCING SAID COMPOSITION THEREOF

(75) Inventors: Chandra Shekhar Nautiyal, Lucknow (IN); Sangeeta Mehta, Lucknow (IN); Harikesh Bahaadur Singh, Lucknow (IN); Palpu Pushpangadan, Lucknow (IN)

(73) Assignee: Council of Scientific and Industrial Research, New Dehli (IN)

( * ) Notice: Subject to any disclaimer, the term of this patent is extended or adjusted under 35 U.S.C. 154(b) by 393 days.

(21) Appl. No.: 10/173,745

(22) Filed: Jun. 19, 2002

(65) Prior Publication Data

US 2003/0211119 A1    Nov. 13, 2003

Related U.S. Application Data

(60) Provisional application No. 60/316,283, filed on Sep. 4, 2001.

(51) Int. Cl.
*C12N 1/20* (2006.01)

(52) U.S. Cl. .................. 424/93.3; 435/252.5; 504/117

(58) Field of Classification Search ............. 435/252.5; 424/93.3

See application file for complete search history.

(56) References Cited

U.S. PATENT DOCUMENTS 2,258,319 A * 10/1941 Dutky ...................... 424/93.46
4,663,162 A *  5/1987 Kado et al. .............. 424/93.46

OTHER PUBLICATIONS

Amethyst Galleries (http://mineral.galleries.com/minerals/silicate/clays.htm).*

* cited by examiner

*Primary Examiner*—Irene Marx
(74) *Attorney, Agent, or Firm*—Birch, Stewart, Kolasch & Birch, LLP

(57) ABSTRACT

The present invention relates to a synergistic composition useful as bioinoculant, said composition comprising bacterial strains of accession Nos. NRRL B-30486, NRRL B-30487, and NRRL-B 30488, individually or in all possible combinations, and optionally carrier, with each of the strains showing plant promotery activity, phytopathogenic fungi controlling activity, abiotic stress conditions tolerating capability, phosphate solubilization capability under abiotic stress conditions; further, a method of producing said composition thereof, and in addition, a method of isolating said bacterial strains from cow 'Sahiwal'.

15 Claims, No Drawings

SYNERGISTIC BIOINOCULANT COMPOSITION COMPRISING BACTERIAL STRAINS OF ACCESSION NOS. NRRL B-30486, NRRL B-30487, AND NRRL B-30488 AND A METHOD OF PRODUCING SAID COMPOSITION THEREOF

This application claims priority on provisional Application No. 60/316,283 filed on Sep. 4, 2001, the entire contents of which are hereby incorporated by reference.

FIELD OF THE PRESENT INVENTION

The present invention relates to a synergistic composition useful as a bioinoculant, said composition comprising bacterial strains of accession Nos. NRRL B-30486, NRRL B-30487, and NRRL-B 30488, individually or in all possible combinations, and optionally a carrier, with each of the strains showing plant growth-promoting activity, phytopathogenic fungi controlling activity, abiotic stress conditions tolerating capability and phosphate solubilization capability under abiotic stress conditions The invention further relates to a method of producing said composition thereof, and in addition, to a method of isolating said bacterial strains from a cow 'Sahiwal'.

BACKGROUND AND PRIOR ART OF THE PRESENT INVENTION

The microbial world is a microcosm whose activities are of central importance to the biosphere. Microbial products contribute to environment, plant, public, and soil health. There is a striking diversity of microorganisms in their ecological and physiological specialization. They have evolved to cope with and flourish in almost every niche, no matter how inhospitable. Microorganisms also form a range of associations with other microbes and with other plants and animals. They can be pathogens, parasites, symbionts, commensales and saprophytes, and thus, their ecological influence infiltrates into all trophic levels of life and gamut of possible ecosystems. Microbes have proved to be an exceptionally rich source of new products, and there is every indication that they will continue to be so in the future. Therefore, exploration of biodiversity for novel microbes that are of ecologically significance or are of economic value is of importance. This has prompted microbiologists to continue to search for novel useful microbes from sources that remain uncharacterized.

According to Hindu mythology as well as the Indian traditional medical practices (both the classical systems like Ayurveda and Siddha and the oral practices of the rural villagers) cow's milk has rejuvenatory health protecting and health promoting properties and hence has been said as the best one among vitalizers [Caraka-Samhita, Editor-translator P. Sharma, Chaukhambha Orientalia, Varanasi, India, volume 1, p. 213 (1981); P. Pushpangadan, Ethnobiology in India: A status report, Ministry of Environment and Forests, Government of India, New Delhi (1994); P. Pushpangadan, All India Coordinated research project on ethnobiology: Final technical report 1982–1998, Ministry of Environment and Forests, Government of India, New Delhi (1998)].

Milk may be defined as the normal secretion of the mammary gland of a mammal. Milk as it is secreted by the gland of mammals is free of microorganisms. However, microorganisms associated with the teat move up the teat canal and into the interior of the udder [J. C. Olsen and G. Mocquot. Milk and milk products. In: International commission on microbiological specifications for foods. Microbial ecology of foods. Food commodities. Vol. 2. New York: Academic Press (1980) pp. 470–486]. This causes even aseptically drawn milk to contain microorganisms, mostly bacteria. Bacteria in aseptically drawn milk are usually limited in number and include mostly micrococci, lactococci, staphylococci, streptococci, and *bacillus* [F. L. Bryan, Journal of Food Protection, Volume 46, pp. 637–649 (1983); R. A. Ledford. Raw milk and fluid milk products. In: Applied dairy microbiology. Eds. E. H. Marth and J. L. Steele, New York: Marcel Dekker, Inc. (1998) pp. 55–64].

It has been known for more than four decades that many of the bacteria that occur commonly in milk find it a relatively unfavorable medium and it would thus appear that milk has pronounced selective properties [T. Gibson and Y. A. Abd-El-Malek, Canadian Journal of Microbiology, Volume 3, pp. 203–213, (1957)]. Thus the bacterial flora that has invaded the teat and/or udder must have the ability to survive and multiply under these sub-optimal conditions. Therefore, work on the milk described in this application pertains to bacterial flora persisting in the teat and/or udder, which have gained entrance into the aseptically drawn milk, in our attempt to search for novel microbes, from an ecological niche that remains uncharacterized.

Improving soil fertility is one of the most common tactics to increase agricultural and forest production. We have isolated bacteria beneficial to plants from cow's milk. Inoculation of seeds or soil with beneficial microorganisms for crop improvement has been practiced for a number of years. A variety of mechanisms have been identified as being responsible for such plant growth promoting activity. For example, certain microorganisms indirectly promote plant growth by inhibiting the growth of deleterious microorganisms; or directly enhance plant growth by producing growth hormones; and/or by assisting in the uptake of nutrients by the crops, e.g., phosphorus (P) [C. S. Nautiyal et al., FEMS Microbiology Letters, Volume 182, pp. 291–296 (2000)].

However, a major factor in the unsuccessful commercialisation of bioinoculants has been the inconsistency of field test results as their establishment and performance are severely effected by environmental factors especially under stress conditions encountered in soil e.g., salt, pH, and temperature [C. S. Nautiyal et al., FEMS Microbiology Letters, Volume 182, pp. 291–296 (2000)]. Therefore, it would be desirable to provide stress tolerant bacterial strains as bioinoculants [C. S. Nautiyal, Biocontrol of plant diseases for agricultural sustainability. In: Biocontrol potential and its exploitation in sustainable agriculture. Volume 1, Eds. R. K. Upahyay, K. G. Mukerji, and B. P. Chamola, Kluwer Academic/Plenum Publishers, New York (2000) pp. 9–23]. Plant growth promoting microorganisms include but are not limited to *Rhizobium, Pseudomonas, Azospirillum*, and *Bacillus* etc. [A. K. Saxena et. al., Bacterial biocontrol agents and their role in plant disease management. In: Biocontrol potential and its exploitation in sustainable agriculture. Volume 1, Eds. R. K. Upadhyay, K. G. Mukerji, and B. P. Chamola, Kluwer Academic/Plenum Publishers, New York (2000) pp. 25–37].

Usefulness of *B. subtilis* as a source of an antagonist for plant pathogenic fungus *Sclerotium rolfsii* is well known [P. Broadbent et al., Australian Journal of Biological Sciences, Volume 24, pp. 975 (1971)]. Baker et al. [Phytopathology, Volume 73, 1148–1152 (1983)] also report on use of *B. subtilis* as a biocontrol agent of fungal plant pathogens. Pusey et al. [Plant Disease, Volume 72, pp. 622–626 (1988)] and P. L. Pusey [U.S. Pat. No. 5,047,239] disclosed control of post harvest fruit rot using *B. subtilis*. S. D. Heins et al.

[U.S. Pat. No. 6,103,228] have disclosed methods of protecting or treating plants from fungal and bacterial infections and corn rootworm infestations using *B. subtilis*.

*B. lentimorbus* is the causative agent of milky disease in Japanese beetle and related scarab larvae [K. E. Rippere et al. International Journal of Systematic Bacteriology, Volume 48, pp. 395–402 (1998)], and therefore is used for the biocontrol of larvae of certain insects [R. E. Gordon et al., The genus *Bacillus*, Agriculture handbook no. 427, United States Department of Agriculture, U.S. Government printing office, Washington D.C. (1973)]. *B. lentimorbus* has also been used to increase the production of fish [W. T. Logan et al., U.S. Pat. No. 5,746,155] and to treat poultry litter [W. T. Logan et al., U.S. Pat. No. 6,017,525].

For propagating bacteria commonly used carriers for commercial inoculants are vermiculite, charcoal, caboxymethyl cellulose, peat, perlite, polyvinyl-pyrrolidone, and talc. Press mud, a "waste" product obtained during sugar manufacture, has also been used as a carrier for *Azotobacter chroococcum* and *Rhizobium japonicum* [K. S. Jauhri, Indian Journal Agriculture Research, Volume 24, pp. 189–197 (1990)]. Press mud, like any other organic material, affects the physical, chemical and biological properties of the soils. It also helps to increase water stable aggregates in soils. It can be composted with distillery spent wash and utilized as a better organic material than press mud alone [D. P. Yadav. Recycling of sugar factory press mud in agriculture. In: Recycling of crop, animal, human, and industrial wastes in agriculture. Ed. H. L. S. Tandon, Fertilizer development and consultation organization, New Delhi (1995) pp. 91–108]. Agricultural and environmental industries would therefore clearly benefit from a simple, less expensive method of making microbial inoculants for plants, seeds and soil.

While work on the microbiology of milk so far has been on psychrotrophic bacteria because of their importance in milk and dairy products [M. A. Cousin. Journal of food protection. Volume 45, pp. 172–207 (1982); R. A. Ledford. Raw milk and fluid milk products. In: Applied dairy microbiology. Eds. E. H. Martha and J. L. Steele, New York: Marcel Dekker, Inc. (1998) pp. 55–64], no bacterial strain has been previously found from the milk of cows which has the ability to control phytopathogenic fungi, promote plant growth, provide tolerance for abiotic stresses, and solubilize phosphate under abiotic stress conditions.

India is one of the few countries in world that has contributed richly to the international livestock gene pool and improvement of animal population in the world. Cattle and buffalo contribute nearly 15% of the gross national income. The country possesses 23% of the world bovine population. "Cattle" is a common term for the domesticated herbivorous mammals that contribute to genus *Bos*, of the family Bovidae. Modern cattle are divided into two species: *B. taurus*, which originated in Europe and includes most modern breeds of dairy and beef cattle, and *B. indicus*, which originated in India and is characterized by a hump and the withers. The latter are now widespread in Africa and Asia, with lesser numbers imported to North America (primarily in the southern U.S.), Central America, and Northern and Central America.

Dairy cattle are those breeds that have been developed primarily to produce milk. In North America the major breeds of dairy cattle are the Holstein-Friesian, Ayrashire, Brown Swiss, and Jersey. Among the major dairy breeds of *B. indicus* found primarily in India are the Gir, Hariana, Red Sindhi, Tharparker, and Sahiwal. By far Sahiwal is the best breed of the subcontinent. It is comparatively a heavy breed with a symmetrical body and loose skin, when compared with Red Sindhi that it closely resembles. The animals are usually long and fleshy and with a heavier build. The color is redish dun or pale red, sometimes fleshed with white patches. A number of herds of this breed are maintained in India. The milk yield ranges from 1400 to 2500 kg. The heritability of this trait is 0.2 to 0.3. The age at first calving ranges from 37 to 48 months and the calving interval is from 430 to 580 days. Sahiwal is one of the most popular breeds of the subcontinent. It has been exported to Sr. Lanka, Kenya and many countries in Latin America and the West Indies where a new breed called Jamaica Hope has been evolved out of Sahiwal and Jersey crossbreeds [P. N. Bhat, Handbook of Animal Husbandry, Directorate of Publication and Information on Agriculture, Krishi Anusandhan Bhawan, Pusa, New Delhi (1997)].

Accordingly, there has been no clear indication heretofore that any bacteria isolated from cows might act as a biocontrol agent, and certainly no showing of direct, bacterial-mediated stimulation of plant growth per se. Nevertheless, a bacterial strain capable of promoting plant growth, tolerance for abiotic stresses, and that solubilizes phosphate under abiotic stress conditions, if one were isolated, could find immediate application, e.g., in soils affected by phytopathogens, poor availability of nutrients like phosphorus, and environment stresses etc. Additionally, no procedure for the selection of such bacterial strain has been reported. We have found by direct comparison on a variety of plant types that the unique combination of selected bacterial strains of the invention is effective in the enhancement of plant growth and health.

The present invention relates to novel strains of bacteria isolated from cows which have the ability to control phytopathogenic fungi, promote plant growth, improve tolerance for abiotic stresses, solubilize phosphate under abiotic stress conditions, and a method for the selection of these strains.

OBJECTS OF THE PRESENT INVENTION

The main object of the present invention is to isolate bacterial strains from cows that are useful as a bioinoculant.

Another main object of the present invention is to isolate bacterial strains from the cow Sahiwal that have plant growth-promoting activity.

Yet another object of the present invention is to isolate bacterial strains from the cow Sahiwal, having plant growth-promoting activity of at least 5% of the dry weight.

Still another object of the present invention is to isolate bacterial stains from the cow Sahiwal showing plant growth promoting activity in terms of less seeding mortality, better seedling germination, plant height, number of pods and seed dry weight.

Still another object of the present invention is to isolate bacterial strains from the cow Sahiwal with phytopathogenic fungi-controlling activity.

Still another object of the present invention is to isolate bacterial strains from the cow Sahiwal that have a phosphate solubilizing property.

Still another object of the present invention is to isolate bacterial strains from the cow Sahiwal having abiotic stress condition tolerating activity.

Still another object of the present invention is to isolate bacterial strains from the cow Sahiwal having 4–8% salt tolerance ability.

Still another object of the present invention is to isolate bacterial strains from the cow Sahiwal having pH 4–10-tolerance ability.

Still another object of the present invention is to isolate bacterial strains from the cow Sahiwal having temperature 50–60° C. tolerance ability.

Still another object of the present invention is to develop a synergistic formulation comprising three strains isolated from the cow Sahiwal with said composition having properties of controlling phytopathogenic fungi, promoting plant growth, having tolerance for abiotic stresses, solubilizing phosphate under abiotic stress conditions and producing anti-fungal metabolites.

Still another object of the present invention is to develop a formulation comprising three strains isolated from the cow Sahiwal, useful as a bioinoculant, showing maximum viability under varied storage or greenhouse or field conditions.

Still another object of the present invention is to develop a formulation comprising the three isolated strains from the cow Sahiwal with accession Nos. NRRL B-30486, NRRL B-30487, and NRRL-B 30488, wherein said formulation can be applied in liquid or dry form to seeds, plants, and soil.

DETAILED DESCRIPTION OF THE PRESENT INVENTION

The present invention relates to a synergistic composition useful as a bioinoculant, said composition comprising bacterial strains of accession Nos. NRRL B-30486, NRRL B-30487, and NRRL-B 30488, individually or in all possible combinations, and optionally a carrier, with each of the strains showing plant growth-promoting activity, phytopathogenic fungi controlling activity, abiotic stress conditions tolerating capability and phosphate solubilization capability under abiotic stress conditions. The invention further relates to a method of producing said composition thereof, and in addition, to a method of isolating said bacterial strains from a cow 'Sahiwal'.

An embodiment of the present invention is a synergistic composition useful as a bioinoculant, said composition comprising bacterial strains of accession Nos. NRRL B-30486, NRRL B-30487, and NRRL-B 30488, individually or in all possible combinations, and optionally a carrier.

The strains NRRL B-30486, and NRRL B-30488 belong to the group *Bacillus lentimorbus*.

The strain NRRL B-30487 belongs to the group *Bacillus subtilis*.

The strain NRRL B-30486 shows the characteristics as listed below:

| Characteristics | NRRL B-30486 |
| --- | --- |
| Shape | Rods |
| Size | |
| Width, μm | 1.5–2.0 |
| Length, μm | 3.0–6.0 |
| Gram reaction | + |
| Catalase reaction | − |
| Anaerobic growth | + |
| Voges-Proskauer Reaction | − |
| pH in V-P broth | 5.5 |
| Acid from | |
| D-glucose | + |
| L-arabinose | − |

-continued

| Characteristics | NRRL B-30486 |
| --- | --- |
| D-xylose | − |
| D-mannitol | − |
| Gas from glucose | + |
| Hydrolysis of | |
| Casein | − |
| Gelatin | − |
| Starch | − |
| Use of citrate | − |
| Nitrate to nitrite | − |
| Indole formation | − |
| Growth at pH in nutrient broth | |
| 6.8 | + |
| 5.7 | + |
| Growth in Nacl | |
| 2% | + |
| 5% | + |
| 7% | + |
| 10% | + |
| Growth at | |
| 30° C. | + |
| 40° C. | + |
| 50° C. | + |
| 55° C. | + |
| 65° C. | − |

The strain NRRL B-30487 shows characteristics listed below:

| Characteristics | NRRL B-30487 |
| --- | --- |
| Shape | Oval |
| Size | |
| Width, μm | 2.5 |
| Gram reaction | + |
| Catalase reaction | + |
| Anaerobic growth | − |
| Voges-Proskauer Reaction | + |
| pH in V-P broth | 5.8 |
| Acid from | |
| D-glucose | + |
| L-arabinose | + |
| D-xylose | + |
| D-mannitol | + |
| Gas from glucose | − |
| Hydrolysis of | |
| Casein | + |
| Gelatin | + |
| Starch | + |
| Use of citrate | + |
| Nitrate to nitrite | + |
| Indole formation | − |
| Growth at pH in nutrient broth | |
| 6.8 | + |
| 5.7 | + |
| Growth in Nacl | |
| 2% | + |
| 5% | + |
| 7% | − |
| 10% | − |

-continued

| Characteristics | NRRL B-30487 |
|---|---|
| Growth at | |
| 30° C. | + |
| 40° C. | + |
| 50° C. | + |
| 55° C. | + |
| 65° C. | − |

The strain NRRL B-30488 shows characteristics listed below:

| Characteristics | NRRL B-30488 |
|---|---|
| Shape | Rods |
| Size | |
| Width, μm | 1.5–2.0 |
| Length, μm | 5.0–10.0 |
| Gram reaction | + |
| Catalase reaction | − |
| Anaerobic growth | + |
| Voges-Proskauer Reaction | − |
| pH in V-P broth | 5.2 |
| Acid from | |
| D-glucose | + |
| L-arabinose | − |
| D-xylose | − |
| D-mannitol | − |
| Gas from glucose | + |
| Hydrolysis of | |
| Casein | − |
| Gelatin | − |
| Starch | − |
| Use of citrate | − |
| Nitrate to nitrite | − |
| Indole formation | − |
| Growth at pH in nutrient broth | |
| 6.8 | + |
| 5.7 | + |
| Growth in Nacl | |
| 2% | + |
| 5% | + |
| 7% | + |
| 10% | + |
| Growth at | |
| 30° C. | + |
| 40° C. | + |
| 50° C. | + |
| 55° C. | + |
| 65° C. | − |

In still another embodiment of the present invention, the carrier is selected from a group comprising vermiculite, charcoal, a mixture of fermented sugar factory sulphitation press mud and distillery spent wash, and sugar factory carbonation press mud.

In still another embodiment of the present invention, the ratio of the three strains is about 1:1:1.

In still another embodiment of the present invention the total concentration of strains is $10^4$ to $10^{10}$ cfu/g of carrier and preferably $10^6$ to $10^8$ cfu/g of carrier.

In still another embodiment of the present invention the concentration of each strain is $10^4$ to $10^{10}$ cfu/g of carrier and preferably $10^7$ to $10^8$ cfu/g of carrier.

In still another embodiment of the present invention, the generation time of the strains is 55–65 minutes at 30° C.

In still another embodiment of the present invention, said strains colonize plant roots.

In still another embodiment of the present invention, said strains survive all the seasons of the plant.

In still another embodiment of the present invention, said strains survive for at least two to three years in the composition.

Another embodiment of the present invention is an in vitro method of isolating bacterial strains of accession nos. NRRL B-30486, NRRL B-30487, and NRRL-B 30488, from the milk of cow 'Sahiwal', said strains having properties of controlling phytopathogenic fungi, promoting plant growth, having tolerance for abiotic stresses, solubilizing phosphate under abiotic stress conditions and producing anti-fungal metabolites. In this embodiment milk is collected from the cow 'Sahiwal'.

In yet another embodiment of the present invention, the milk is plated on a culture medium.

In yet another embodiment of the present invention, the culture is incubated at a temperature of 25–35° C., for about 1–3 days.

In still another embodiment of the present invention, all morphologically distinct bacteria from the culture are selected.

In still another embodiment of the present invention, the strains selected in the previous step which will suppress phytopathogenic fungi are further selected by showing a zone of inhibition of at least 2 mm, by incubating at 30–35° C. preferably 28° C., for 20–35 days, preferably 27 days.

In still another embodiment of the present invention, screening said strains selected in the previous step are selected for plant growth-promoting activity, showing at least a 5% increase in the dry weight of a plant, by growing plants in the presence of selected bacteria in a concentration of bacteria ranging between about $10^6$ to $10^{10}$ cfu/seed or about $10^6$ to $10^8$ cfu/gram of soil.

In still another embodiment of the present invention, the strains selected in the previous step are screened at 4–8% salt stress tolerance for further selection.

In still another embodiment of the present invention, the strains selected in previous step are screened at pH 4–10 stress tolerance for further selection.

In still another embodiment of the present invention, the strains selected in the previous step are screened at 50–60° C. temperature stress tolerance for further selection.

In still another embodiment of the present invention, the strains selected in the previous step are screened for the ability to solubilize phosphate under abiotic stress conditions of high salt, pH, and temperature for further selection.

In still another embodiment of the present invention the desired three bacterial strains are isolated.

In still another embodiment of the present invention, the plant upon which growth-promoting activity is observed is selected from a group comprising *Zea mays, Abelmoschus esculentus, Luffa cylindrica., Lycopersicon esculentum, Abelmoschus esculentus*, and *Cucumis sativus*.

In still another embodiment of the present invention, the culture medium used for growing the bacteria is Nutrient Agar, said medium comprising beef extract (2–10 gms), peptone (5–15 gms), sodium chloride (2–10 gms), agar (10–20 gms), distilled water (about 1.0 L), with pH ranging between 7.0–7.4.

In still another embodiment of the present invention, pH tolerance is tested at 30° C.

In still another embodiment of the present invention, soil moisture ranges between 15–30%, and is preferably 20%.

In still another embodiment of the present invention, the salt is preferably NaCl.

In still another embodiment of the present invention, the strains are grown on Nutrient Broth (NB) medium consisting of Beef extract (0.5%), peptone (1%), NaCl (0.5%), and distilled water, with pH of the medium is 7.2.

In still another embodiment of the present invention, the pathogenic fungus against which the bacteria promote resistance is one from the group comprising *F. moniliforme, C. falcatum, F. oxysporum* f. sp. *ciceri, R. solani, Pythium* sp., *Phoma sorghii, Sclerotium rolfsii, alternaria solani, curvularia lunata, sclerotinia sclerotiorum*, and *aspergillus niger*.

In still another embodiment of the present invention, the concentration of the strains ranges between 4–10 CFU/ml.

In still another embodiment of the present invention, phosphate solubilization increases by about 428% upon a combined increase of temperature, salt, and pH.

In still another embodiment of the present invention, phosphate solubilization increases by about 160% with increase in salt concentration.

In still another embodiment of the present invention, phosphate solubilization increases by about 130% with increase in pH.

In still another embodiment of the present invention, strains are selected for high pH stress tolerance at preferably pH 9.

In still another embodiment of the present invention, strains are selected for 55° C. temperature stress tolerance.

In still another embodiment of the present invention, the selected bacteria are those demonstrating the best results in terms of less seedling mortality, and better seedling germination, plant height, number of pods and seed dry weight.

In still another embodiment of the present invention, plant growth-promoting activity goes up by 3–400%.

In still another embodiment of the present invention, the concentration of fungi ranges between 4–7 spores/ml of culture medium.

In still another embodiment of the present invention, abiotic stress conditions for solubilization of phosphate are selected from a group of conditions comprising high pH ranging between 7–9, high temp ranging between 30–45, and salt concentration ranging between 0.1–4%.

Another embodiment of the present invention is a method of preparing a plant growth-promoting formulation comprising bacterial strains of accession Nos. NRRL B-30486, NRRL B-30487, and NRRL-B 30488, individually or in all possible combinations, and a carrier.

Another embodiment of the present invention comprises growing bacteria in a culture, individually to a concentration of about $10^8$ to $10^{11}$ cfu/ml, preferably $10^9$ to $10^{10}$ cfu/ml, optionally followed by mixing the cultures in equal ratio in case of preparing a consortium.

In still another embodiment of the present invention, the culture is diluted with water in the ratio of 1:50 to 1:150, preferably 1:100, containing approximately $10^8$ to $10^9$ cfu/ml of bacteria.

In still another embodiment of the present invention, about 1–3 liter of the culture/ton of freshly homogenized carrier, preferably 2 liter of the culture/ton of freshly homogenized carrier, is sprayed onto soil and mixed.

In still another embodiment of the present invention, windrows are churned daily at least twice a day for about 2 days, to increase the temperature of the windrows up to 70–75° C.

In still another embodiment of the present invention, spent wash or water is sprayed into the churning windrow for about 40 days to maintain moisture level of about 55–65%.

In still another embodiment of the present invention, the windrows are churned further for another 3–5 days, now to reduce the moisture and temperature of the fermented product to about 30% and 40–45° C.

In still another embodiment of the present invention, the plant growth promoting bioinoculant is packaged ready for its application.

In still another embodiment of the present invention, the carrier is selected from a group comprising fresh sulphinated press mud and carbonation press mud.

In still another embodiment of the present invention, the culture medium for growing the bacteria is NB medium.

In still another embodiment of the present invention, the mixture is homogenized manually and by using an aero tiller.

In still another embodiment of the present invention, the formulation demonstrates maximum viability, under varied storage or greenhouse or field condition.

In still another embodiment of the present invention, the ratio of the bacterial strains is about 1:1:1.

In still another embodiment of the present invention, the formulation is used on plants, seeds, and soil.

Still another embodiment of the present invention is a method of using a plant growth-promoting formulation comprising bacterial strains of accession Nos. NRRL B-30486, NRRL B-30487, and NRRL-B 30488, individually or in all possible combinations, and a carrier, said method comprising steps of applying the said bioinoculant in a liquid or dry form to seeds, plants, and soil.

In still another embodiment of the present invention, the bioinoculant also contains gums or sugars to improve adhesion.

In still another embodiment of the present invention, plants of the variety are tested for plant growth promotion in the field in the presence of bacteria in a concentration of about $10^7$ to $10^9$ cfu/seed or about $10^6$ to $10^8$ cfu/gram of soil.

In still another embodiment of the present invention, the formulation is used alone or in combination with other chemicals that are harmless to the growth and survival of bacteria.

In still another embodiment of the present invention, the chemicals used are selected from a group comprising pesticides, fertilizers, nematicides, and herbicides, with or without for example, lime pelleting, to limit the severity of the effect of these materials.

Still another embodiment of the present invention is the method of making a composition useful as bioinoculant, said composition comprising one or more of novel bacterial strains of accession Nos. NRRL B-30486, NRRL B-30487, and NRRL-B 30488 and a carrier.

In still another embodiment of the present invention, the bacterial strains are cultured in a growth medium to log phase.

In still another embodiment of the present invention, the culture is diluted with water in the ratio ranging between 1:10 to 1:100000, with preferable ratio of 1:100.

In still another embodiment of the present invention, the diluted culture is mixed with an inert powdered carrier, with the moisture level of the mixture ranging between 20–40%, preferably about 30% on a wet basis.

In still another embodiment of the present invention, the mixture is incubated for at least about two days, maintaining constant moisture level in said mixture.

In still another embodiment of the present invention, the bacteria count in the mixture is increased to a range of about $10^4$ to $10^{10}$/g of carrier.

In still another embodiment of the present invention, the survival rate of the bacteria is monitored over the period of at least one year in the composition, wherein the bacterial strains are present preferably in a range from about $10^7$ to $10^9$ cfu/g of carrier, thus showing a long survival rate of microbes as inoculate.

In still another embodiment of the present invention, the carrier is selected from a group comprising vermiculite, charcoal, a mixture of fermented sugar factory sulphitation press mud and distillery spent wash, and sugar factory carbonation press mud, rice husk, carboxymethyl cellulose, peat, perlite, talc, and polyvinyl pyrrolidone.

In still another embodiment of the present invention, preferred carriers are selected from a group comprising vermiculite, charcoal, and fermented press mud.

In still another embodiment of the present invention, the bacterial count is most preferably about $10^8$ cfu/g of carrier.

In still another embodiment of the present invention, plants for growth promotion are selected from a group comprising chickpea, *A. esculentus*, and *C. sativus*, and *Z. mays*, and *Triticum aestivum*, and *Glycine max*, and *Pisum sativum*, and *Impatiens balsamina*.

In still another embodiment of the present invention the ratio of strains is about 1:1:1, in the case of a consortium.

In still another embodiment of the present invention, growth medium for culturing bacteria is NB medium.

In still another embodiment of the present invention, bacterial strains are grown individually to a concentration of about $10^9$ to $10^{10}$ cfu/ml followed by mixing the cultures in the ratio of about 1:1:1.

In still another embodiment of the present invention, the culture is diluted with water preferably in the ratio of 1:10, containing approximately $10^8$ to $10^9$ cfu/ml.

In still another embodiment of the present invention, moisture of the product is regulated with windrows.

Applicants have discovered a novel method for screening bacteria to select those bacterial strains that have the ability to control phytopathogenic fungi, promote plant growth, tolerance for abiotic stresses, and solubilize phosphate under abiotic stress conditions. When used as bioinoculants, the novel bacteria obtained by our method have the ability to control phytopathogenic fungi and promote plant growth under field conditions.

Applicants have also discovered three novel strains of *Bacillus*, when used individually or as a novel blend of consortium which provides a unique synergism, that have the ability to control phytopathogenic fungi under field conditions, promote plant growth under field conditions, tolerance for abiotic stresses, and solubilize phosphate under abiotic stress conditions.

Screening Method:
1. Isolating strains of bacteria from milk and selecting the bacteria having potential for suppressing growth of phytopathogenic fungi *Colletotrichum falcatum, Sclerotium roltsii, Alternaria solani, Penicillium* sp., *Pythium aphanidermatum, Phytophthora palmivora, Curvularia lunata, Sclerotinia sclerotiorum*, and *Aspergillus niger*, under in vitro conditions on nutrient agar plates (NA) by streaking one to four single bacterial colonies around the edge of a 90-mm diameter petri plate and incubating it at 28° C. for two days; transferring an agar plug inoculum of the fungi (5-mm square) to the centre of the plate individually from a source plate of fungi to be tested on NA for 2 to 7 days; and selecting the bacterial strains having the biocontrol activity which inhibited fungal growth.
2. Screening of bacteria selected in step 1 having potential for suppressing growth of pathogenic fungi under in vitro conditions, in the greenhouse for plant growth-promoting bacteria as follows: growing maize plants in the presence of bacteria selected in step 1 in the greenhouse in a concentration of about $10^8$ colony forming units (cfu)/ seed in non-sterile soil; growing control maize plants as above but without addition of the bacteria; and selecting as plant growth promoting bacteria those strains which cause the treated plants to exhibit greater dry weight.
3. Screening of bacteria selected in step 2 as plant growth promoters for abiotic stress (salt, pH, and temperature) tolerance under in vitro conditions as follows: selecting as stress tolerant bacteria those strains selected in step 2 which exhibit tolerance to 6% salt (NaCl), 5–9 pH, and 55° C. temperature.
4. Characterization of bacteria selected in step 3 tolerant for abiotic stress for ability to solubilize phosphate under abiotic stress (salt, pH, and temperature) conditions as follows: quantitative estimation of phosphate solubilization in broth using National Botanical Research Institute's phosphate growth medium (NBRIP); elucidating effect of salt (NaCl), pH, and temperature on solubilization of phosphate by growing the strains on NBRIP containing various amounts of NaCl (w/v), pH, and temperature as indicated; inoculating NBRIP medium with approximately $10^9$ cfu/ml of the bacterial strain; autoclaved uninoculated medium served as controls.
5. Screening of bacteria selected in step 3 tolerant for survival in carriers, for its commercial use as a bioinoculant, as follows: culturing the bacteria in a growth media; adding log-phase cells to various carriers, particularly such as vermiculite, charcoal, and fermented press mud; thereafter applying the inoculum to seeds (e.g., by preparing a slurry containing the carrier/bacteria mixture and gums or sugars to improve adhesion) or by directly applying to soil or, by dripping carrier/bacteria suspensions into planting furrows or by mixing with other planting material; using the formulation demonstrating maximum viability (under varied storage or greenhouse or field condition) for plants, seeds, and soil.
6. Field trial of bacteria selected in step 3 tolerant for abiotic stress for ability to control plant pathogens, particularly fungi, such as *Fusarium oxysporum* f. sp. *ciceri* i.e., reduce incidence or severity of the disease on field grown chickpea and for ability to control plant pathogens, particularly fungi, such as *Fusarium moniliforme* and *Colletotrichum falcatum* on field grown sugarcane, using various carriers such as vermiculite.
7. Field trial of bacteria selected in step 3 tolerant for abiotic stress for ability to promote plant growth of field grown plants such as sugarcane, using various carriers such as vermiculite and fermented press mud.

The bacterial strains selected by the above process have the ability to control phytopathogenic fungi, promote plant growth, tolerance for abiotic stresses, and solubilise phosphate under abiotic stress conditions.

In accordance with this discovery, It is an object of the invention to provide a method for selecting those strains which have the ability to control phytopathogenic fungi, promote plant growth, tolerance for abiotic stresses, and solubilize phosphate under abiotic stress conditions, using the so-selected bacterial strains.

It is also an object of the invention to provide a means for screening bacteria to select those strains that have the ability to control phytopathogenic fungi and promote plant growth under field conditions.

A further object of the invention is the provision of novel strains of *B. lentimorbus* and *B. subtilis* that have the ability to control phytopathogenic fungi, promote plant growth, tolerance for abiotic stresses, and solubilize phosphate under abiotic stress conditions.

Another object of the invention is the provision of suitable carriers for bacterial strains, in particular, novel strains of *B. lentimorbus* and *B. subtilis* selected in step 3 for survival in various carriers, for commercial production as bioinoculant for plants, seeds, and soil.

Yet another object of the invention is the provision of novel strains of *B. lentimorbus* and *B. subtilis* that have the ability to control phytopathogenic fungi under field conditions.

Still another object of the invention is the provision of novel strains of *B. lentimorbus* and *B. subtilis* that have the ability to promote plant growth under field conditions.

Other objectives and advantages of the invention will become apparent from the ensuing description. It should be understood, however, that the detailed description and the specific examples, while indicating preferred embodiments of the invention, are given by way of illustration only, since various changes and modifications within the spirit and scope of the invention will become apparent to those skilled in the art from this detailed description.

In this description, the term "bacteria from milk" is used to denote bacteria, which have gained entrance into the aseptically drawn milk, by invading the teat and/or udder and have the persistence ability for survival and multiplication under these suboptimal conditions. Therefore, the bacteria described in this application pertain to bacterial flora persisting in the teat and/or udder which represents an ecological niche that remains uncharacterized.

It has been discovered that the proportion of bacterial strains showing biocontrol activity against phytopathogenic fungi was maximum in the milk of Sahiwal cow, followed by human, Holstein cow and buffalo. From this parameter milk of Sahiwal cow was superior to human, Holstein cow and buffalo. Extensive selections from a large number of bacterial strains collected from the milk of human, Sahiwal cow, Holstein cow and buffalo have shown that some of these strains, as described below, have the ability to stimulate plant growth.

Therefore one aspect of the present invention relates to method for screening useful bacteria from the milk of human, Sahiwal cow, Holstein cow and buffalo and application thereof for promoting plant growth.

First the bacteria are isolated by standard procedures such as described in Eklund and Lankford, Laboratory manual for general microbiology [Prentice-Hall, Inc., USA (1967), pp. 21–27]. For example, serial dilutions of the milk samples are prepared and may be spread-plated on various general media. Examples of general media, which propagate a broad number of bacteria, include NA and the like. Next the NA plates are incubated for 1 to 3 days at a temperature suitable for bacterial growth, generally about 25 to 35° C. The preferred temperature for incubation of plates is 30° C.

Next, individual strains of the bacteria are subjected to a first screening for selecting bacteria having potential for suppressing phytopathogenic fungi under in vitro conditions as described earlier [C. S. Nautiyal, Current Microbiology, Volume 35, pp. 52–58 (1997)]. Bacterial colonies on NA plates were streaked around the edge of a 90-mm diameter petri plate and the plates were incubated at 25–35° C. for 1 to 2 days. An agar plug inoculum of the fungi to be tested (5-mm square) was then transferred to the center of the plate individually from a source plate of the fungi. After incubation for 5 to 7 days inhibition zones were readily observed in the case of bacterial strains having the biocontrol activity.

Choice of time for incubation of the bacterial colonies on the plates before challenging with the pathogenic fungi to be tested and the time of incubation of the plates later on to observe the inhibition zone depends upon the rate of growth of the pathogenic fungi to be tested. For example if the fungus grows fast, e.g., *Rhizoctonia*, then it is preferred that bacterial colonies on NA plates are streaked around the edge of a 90-mm diameter petri plate at least for 2 days in advance before an agar plug inoculum of the fungus to be tested is transferred to the center of the plate. On the contrary, if the fungus is a slow grower e.g., *Fusarium*, then it is preferred that an agar plug inoculum of the fungus to be tested is transferred to the center of the plate and the plates are incubated for 2 to 3 days to allow sufficient time for the fungus to grow, before the bacterial colonies on NA plates are streaked around the edge of the petri plate.

Bacterial strains isolated in the previous step are screened to select those that at a particular concentration promote plant growth under greenhouse conditions as described earlier [C. S. Nautiyal, Current Microbiology, Volume 34, pp. 12–17 (1997)]. In this test sterilized seeds of maize are grown in non-sterilized soil and inoculated with the bacterial strains, individually, at a concentration of $10^6$ to $10^{10}$ cfu/seed. The preferred concentration of inoculum is $10^8$ cfu/seed. Trays (35×35 cm.) with 16 (4×4) places per tray (each space was of 7 cm. width, 10 cm. depth and 1 cm. apart from each other) have been found to be of a convenient size to grow maize and other plants for the greenhouse test. Each place was filled up to 8 cm with non-sterilized soil. Although sterile soil or any other plant growth supporting material for example like vermiculite may also be used instead of non-sterile soil, it is preferred that non-sterile soil from the field where these bacteria are intended to be released is used in a greenhouse test.

Tap water was added to each hole before planting seeds to adjust the soil to 15 to 30% moisture. Preferred soil moisture is 20%. Four bacterial-treated seeds were added per hole. The experiment in the greenhouse was carried out in four different sets of 16 maize seedlings each, for non-bacterized (control) and bacterized (treated) seeds. In each set, data of 21-days-old seedlings was recorded with respect to an average dry weight of 16 plants. In order for the bacterial strain to be considered as plant growth promoter, the seedlings treated with the bacteria must have averaged at least 10% higher dry weight than comparable non-bacterized plants.

The bacterial strains thus selected were further subjected to abiotic stress tolerance by first screening for their ability to grow in nutrient broth (NB) containing 6% salt (NaCl; pH 7 and 30° C. temperature), overnight (14–16 hrs) on a New Brunswick Scientific, USA, Innova Model 4230 refrigerated incubator shaker at 180 rpm. The strains tolerant to 6% salt were grown at 9 pH (6% NaCl and 30° C. temperature), and finally the strains tolerant to 6% salt and pH 9 were grown at 55° C. temperature. Viable cells were counted by removing samples at various times in the presence or absence of stress, as indicated. Serial dilutions of each sample were spotted (25 μl) onto NA plates, and incubated at 30° C. in triplicate as described earlier [C. S. Nautiyal et al., FEMS Microbiology Letters, Volume 182, pp. 291–296 (2000)]. Viable cells were counted after 2–3 days.

The 3 bacterial strains tolerant to abiotic stresses (salt, pH, and temperature) selected as above were further screened for their ability to solubilize phosphate under abiotic stress conditions. Quantitative estimation of phosphate solubilization in broth was carried out using National Botanical Research Institute's phosphate growth medium (NBRIP) as described earlier [C. S. Nautiyal, FEMS Microbiology Letters, Volume 170, pp. 265–270 (1999)].

The effect of salt (NaCl), pH, and temperature on solubilization of phosphate was tested by growing the bacteria on NBRIP in the presence of NaCl, pH, and temperature, as mated using the Fiske and Subbarow method [C. H. Fiske and Y. Subbarow, Journal of Biological Chemistry, Volume 66, pp. 375–400 (1925)].

The subject strains *Bacillus lentimorbus* NBRI0725, *Bacillus subtilis* NBRI1205, and *Bacillus lentimorbus* NBRI3009 have the taxonomic characteristics listed in Table 1, as compared to those of prior art strains of *B. lentimorbus* and *B. subtilis*.

Comparison of biochemical and physical characteristics of *B. lentimorbus* NBRI0725 (invention), *B. lentimorbus* NBRI3009 (invention), *B. lentimorbus* (descriptive), *B. subtilis* NBRI1205 (invention), and *B. subtilis* (descriptive).

|  | *Bacillus lentimorbus* | | | *Bacillus subtilis* | |
| --- | --- | --- | --- | --- | --- |
| Characteristics | NBRI 0725 Invention | NBRI 3009 Invention | Descriptive* | NBRI 1205 Invention | Descriptive |
| Shape | Rods | Rods | Rods | Oval | Rods |
| Size | | | | | |
| Width, μm | 1.5–2.0 | 1.5–2.0 | 0.5–0.7 | 2.5 | 0.7–0.8 |
| Length, μm | 3.0–6.0 | 5.0–10.0 | 1.8–7.0 | 2.0–3.0 | |
| Gram reaction | + | + | + | + | + |
| Catalase reaction | – | – | – | + | + |
| Anaerobic growth | + | + | + | – | – |
| Voges-Proskauer | | | | | |
| Reaction | – | – | – | + | + |
| pH in V-P broth | 5.5 | 5.2 | 5.9–6.9 | 5.8 | 5.0–8.0 |
| Acid from | | | | | |
| D-glucose | + | + | + | + | + |
| L-arabinose | – | – | – | + | + |
| D-xylose | – | – | – | + | + |
| D-mannitol | – | – | – | + | + |
| Gas from glucose | + | + | + | – | – |
| Hydrolysis of | | | | | |
| Casein | – | – | – | + | + |
| Gelatin | – | – | – | + | + |
| Starch | – | – | – | + | + |
| Use of citrate | – | – | – | + | + |
| Nitrate to nitrite | – | – | – | + | + |
| Indole formation | – | – | – | – | – |
| Growth at pH in nutrient broth | | | | | |
| 6.8 | + | + | – | + | + |
| 5.7 | + | + | – | + | + |
| Growth in NaCl | | | | | |
| 2% | + | + | – | + | + |
| 5% | + | + | – | + | + |
| 7% | + | + | – | – | + |
| 10% | + | + | – | – | ND |
| Growth at | | | | | |
| 30° C. | + | + | + | + | + |
| 40° C. | + | + | – | + | + |
| 50° C. | + | + | – | + | + |
| 55° C. | + | + | – | + | + |
| 65° C. | – | – | – | – | – |

*= As described in: R. E. Gordon et al., The genus Bacillus, Agriculture handbook no. 427, United States Department of Agriculture, U.S. Government printing office, Washington D.C. (1973;
ND = No data available.

The 3 strains *B. lentimorbus* NBRI0725, *B. subtilis* NBRI1205, and *B. lentimorbus* NBRI3009 isolated from Sahiwal cow selected by the method of screening as described above have the ability to control phytopathogenic fungi, promote plant growth, tolerance for abiotic stresses and solubilize phosphate under abiotic stress conditions. *B. lentimorbus* NBRI0725, *B. subtilis* NBRI1205, and *B. lentimorbus* NBRI3009 have been deposited under the Budapest treaty on $5^{th}$ of July, 2001 into ARS Patent culture collection, United States Department of Agriculture, 1815 North University Street, Peoria, Ill. 61604, U.S.A. The bacterial strains *B. lentimorbus* NBRI0725, *B. subtilis* NBRI1205, and *B. lentimorbus* NBRI3009 have been allotted following NRRL number *B. lentimorbus* NRRL B-30486, *B. subtilis* NRRL B-30487, and *B. lentimorbus* NRRL B-30488, respectively.

In addition to the other properties noted above, the unexpected and surprising attributes of these specific *B. lentimorbus* and *B. subtilis* strains include the following characteristics. All the three strains have been isolated from the milk of Sahiwal cow. The strains have a rapid generation time in culture (55–65 minutes at 30° C.). In pure culture the strains inhibit the growth of many pathogenic fungi of plants. The strains are capable of colonizing plant roots. These bacteria reduce plant disease in soil both under greenhouse and field conditions. The strains of the present invention are capable of promoting plant growth of plants in soil both under greenhouse and field conditions. Moreover the strains continue to survive in the soil throughout the growing season of the plant.

The subject *Bacillus* strains also has tolerance to abiotic stresses like 6% salt (NaCl), 5–9 pH, and 55° C. temperature.

The subject *Bacillus* strains have the ability to solubilize phosphate under abiotic stress conditions e.g., 0–4% salt (NaCl), 7–9 pH, and 30–45° C. temperature. Phosphate solubilization activity of the strains is induced in the presence of high salt, high pH, and high temperature.

It is within the compass of the invention to isolate any type of bacteria having the ability to control phytopathogenic fungi, promote plant growth, tolerance for abiotic stresses, and solubilize phosphate under abiotic stress conditions, however, *Bacillus* are the bacteria of choice because (1) they can easily be isolated, cultured and identified; (2) being a naturally occurring isolate or strain does not require genetic engineering to be effective; (3) being nutritionally versatile are able to utilize large number of organic substrates, including root exudates; (4) being suppressive to one or more pathogenic fungi; (5) having a stage in its life cycle that is resistant to harsh environmental conditions; (6) being tolerant to abiotic stresses (high salt, high pH, and high temperature); (7) being able to solubilize phosphate under abiotic stress (high salt, high pH, and high temperature) conditions; (8) colonizing the rhizosphere of the root system of the host plant(s) for the full growing season in the field; (9) enhancing the yield of the host plant(s) under field conditions; and (10) being relatively easy to develop for commercial purposes.

Another aspect of the invention is directed to a method of controlling plant diseases and promoting growth of plants in soil both under greenhouse and field conditions. The three bacterial strains designated *B. lentimorbus* NRRL B-30486, *B. subtilis* NRRL B-30487, and *B. lentimorbus* NRRL B-30488 are especially preferred in this process. An inoculant of the subject strain is used such that colonization is in the range of about $10^4$ to $10^{10}$ colony forming units/gram (cfu/g) root occurs and preferably $10^6$ to $10^8$ cfu/g. A mixture of the three strains (consortium) designated *B. lentimorbus* NRRL B-30486, *B. subtilis* NRRL B-30487, and *B. lentimorbus* NRRL B-30488 in the ratio of 1:1:1, consisting of about $10^6$ to $10^{10}$ cfu/ml each and preferably $10^7$ to $10^8$ cfu/ml each is especially preferred in this process. The inoculum can be applied directly to the seeds or plants, can be present in the soil before planting or can be distributed, e.g., by spreading, dusting or the like, over the crop or soil top or in soil furrow where the crop has been planted.

Seeds can be treated by coating with a composition containing the subject bacteria by dipping in a liquid containing these bacteria, by spraying with the liquid, or other method known in the art for applying bacteria to seeds.

According to yet another aspect of the invention cultures of *B. lentimorbus* NRRL B-30486, *B. subtilis* NRRL B-30487, and *B. lentimorbus* NRRL B-30488 may be grown individually in molasses diluted with water in the ratio of 1:1 to 1:10. However dilution of 1:5 is especially preferred in this process. The bacterial strains may be used individually, or as a consortium in the ratio of 1:1:1, consisting of about $10^6$ to $10^{11}$ cfu/ml each and preferably $10^8$ to $10^9$ cfu/ml each is especially preferred in this process. The consortium thus obtained may further be diluted with water in the ratio of 1:10 to 1:10000. However dilution of 1:100 is especially preferred in this process.

Growing the bacteria in molasses makes the process economically very viable. Bacteria grown in such manner may further be used to treat seeds by coating with a composition containing the subject bacteria by dipping in a liquid containing these bacteria, by spraying with the liquid, or other method known in the art for applying bacteria to seeds.

According to a further aspect the invention, the process of the invention may be used with any kind of bacteria or other microorganisms capable of surviving under abiotic stress conditions e.g., tolerance to salt, pH, and temperature. Of particular interest are bacteria, which have biocidal properties, e.g., biofungicidal, pesticidal, and other properties; promote plant growth, and solubilise phosphate under abiotic stress conditions, e.g., high salt, high pH, and high temperature that are capable of living in the soil in the presence of the plants.

The carriers that may be used to disperse the subject strains would include all those commonly used for inoculating crops and would include carriers such as rice husk, carboxymethyl cellulose, peat, perlite, polyvinyl-pyrrolidone, and talc. The bacteria in such compositions are at a level of about $10^4$ to $10^{10}$ cfu/g carrier. Carriers such as vermiculite or charcoal or fermented press mud are especially preferred in this process. The bacteria are grown in broth to the necessary amount, and then mixed with the carrier at the desired inoculum, followed by curing of the mixture by well-known methods.

According to this embodiment of the invention the optimum carrier may vary depending on the bacteria used. Any of the above compositions, liquids, powders, peat, soil, vermiculite, charcoal, fermented press mud and the like may have nutrients included therein or appropriate carrier medium such as water, oils or solid bases such as powders, peat, soil, vermiculite, charcoal, fermented press mud and any other carrier agents. However, as demonstrated by the examples below, vermiculite, charcoal, fermented press mud are preferred.

A further aspect of this invention relates to a process whereby the synergistic composition of the present invention thus produced may be used in any manner known in the art for example, including pretreatment of soil or seeds or pregerminated plant roots alone or in combination with other chemicals which are harmless to the growth and survival of bacteria, for example plant growth promoting compounds, pesticides, fertilizers, nematicides, herbicides, with or without for example, lime pelleting, to limit the severity of the effect of these materials. However, as demonstrated by the example below, compatible pesticides are preferred.

The examples given below in a nonlimiting way will make it possible to better understand the invention.

EXAMPLE 1

Isolation of Bacterial Strains from Milk

Fifty bacterial representatives of the predominant morphologically distinct colonies present on the plates were selected from three individual milk samples from each of healthy human, indigenous (Sahiwal) cow, exotic (Holstein Frisian) cow and buffalo. Therefore, a total of 600 bacterial strains were collected for further screening. Human milk was collected from three mothers with breast-fed infants in the range of 6 to 12 weeks old. Milk from pure breed native Sahiwal cows #12, #217, and #249 was collected from Gajaria farm, Department of Animal Husbandry, Government of Uttar Pradesh, Lucknow. Milk from exotic breed Holstein Frisian (15/16) cows #154, #412, and #667 was collected from Indian Military Farm, Central Command Headquarters, Indian Army, Lucknow. Milk samples from buffalo were collected from local commercial dairy farm. Milk was collected in sterile containers after taking due care to sanitize the teat and human handler. Samples of milk were collected in morning, midway from the milk stream coming out of the teat directly into a sterile container, without having any contact and stored in an ice box during its transportation. Serial dilution of the milk samples were then plated within two hours of collection on Nutrient agar (NA) plates (Beef extract 5.0 gm, peptone 10.0 gm, sodium chloride 5.0 gm, agar 15 gm, distilled water 1000 ml, pH 7.2).

Pure isolates of the individual strains of bacteria representative of the predominant morphologically distinct colonies present on the plates were selected at random and purified by sub-culturing an individual strain on NA plates to obtain a pure culture. Each isolate was stored in an aqueous solution of 30% glycerol at −25° C.

Total bacterial counts from three individual milk samples collected from healthy human, Sahiwal cow, Holstein cow were $10^3$ cfu/ml, compared with a log unit higher of $10^4$ cfu/ml from buffalo (Table 2).

TABLE 2

| | Milk sample from | | | |
|---|---|---|---|---|
| Parameter | Human | Sahiwal cow | Holestien cow | Buffalo |
| Bacteria [cfu/ml] | Log 3.2 | Log 3.1 | Log 3.2 | Log 4.2 |

EXAMPLE 2

Screening of Bacterial Strains under In Vitro Conditions for Ability to Suppress Pathogenic Fungi and Bacteria The 600 bacterial strains obtained by the procedure outlined in Example 1 were screened for their ability to inhibit growth of *Colletotrichum falcatum, Sclerotium rolfsii, Alternaria solani, Penicillium* sp., *Pythium aphanidermatum, Phytophthora palmivora, Curvularia lunata, Sclerotinia sclerotiorum,* and *Aspergillus niger* under in vitro conditions as follows: Four single bacterial colonies on NA plates were streaked around the edge of a 90-mm diameter petri plate and the plates were incubated at 28° C. for two days. An agar plug inoculum of the fungus to be tested (5-mm square) was then transferred to the center of the plate individually from a source plate of the fungus. After incubation for 5 to 7 days inhibition zones were readily observed in the case of bacterial strains having biocontrol activity, as the fungal growth around the streak was inhibited. In case of bacterial strains not having biocontrol activity, fungal growth around the streak was not inhibited and the fungi grew towards the edge of the plate (Table 3). Strains that show a zone of inhibition of at least 2 mm were selected as positive and used for further work.

TABLE 3

| | % of biocontrol bacteria | | | |
|---|---|---|---|---|
| Pathogenic fungi | Human | Sahiwal cow | Holestien cow | Buffalo |
| *Colletotrichum falcatum* | 0 | 17 | 0 | 8 |
| *Sclerotium rolfsii* | 0 | 8 | 0 | 0 |
| *Alternaria solani* | 8 | 8 | 8 | 8 |
| *Penicillium* sp. | 8 | 0 | 0 | 0 |
| *Pythium aphanidermatum* | 8 | 8 | 8 | 0 |
| *Phytophthora palmivora* | 8 | 8 | 8 | 0 |
| *Curvularia lunata* | 17 | 8 | 8 | 0 |
| *Sclerotinia sclerotiorum* | 0 | 17 | 8 | 0 |
| *Aspergillus niger* | 0 | 17 | 8 | 0 |

It was discovered that the percentage of bacterial strains showing biocontrol activity against phytopathogenic fungi was maximum in Sahiwal cow, followed by human, Holstein cow and buffalo. From this parameter milk of Sahiwal cow was superior to human, Holstein cow and buffalo (Table 2). Strains that show a zone of inhibition of at least 2 mm were selected as positive and used for further work.

Of 600 strains tested in vitro, only 150 were determined to be having the biocontrol activity, according to the above criteria.

EXAMPLE 3

Screening of Bacterial Strains for Ability to Promote Plant Growth in Greenhouse The 150 bacterial strains that were suppressive to pathogenic fungi in vitro were screened in a greenhouse by growing bacteria treated maize seeds in non-sterile soil and comparing the treated maize with control maize plants grown without bacterial treatment.

The process of screening of bacterial strains for ability to promote plant growth in a greenhouse of the present invention is disclosed with particular reference to the plant maize. However it should not be inferred that the process of screening of bacterial strains for ability to promote plant growth in greenhouse is restricted to this plant, as any suitable other plant may be employed.

Non-sterile field soil from the farm of National Botanical Research Institute, Lucknow was used to evaluate the plant growth promotion potential of the 150 strains in greenhouse.

A bacterial inoculum for maize seeds was prepared by scraping a culture from plates grown for 48 hours with 10 ml of 0.85% saline water. Maize seeds were surface sterilized by gently shaking (80 R.P.M. on a reciprocal shaker at 28° C.) with 70% ethanol (5 min.), 20% bleach Chlorox (10 min.), followed by three rinses in sterile water. After surface sterilization seeds were soaked in the bacterial suspension for 4 h at 28° C. on a reciprocal shaker at 100 R.P.M. Control seeds (non bacterized) were soaked in 0.85% saline water washed from uninoculated plates. Bacterization levels of seeds were determined by agitating 4 seeds from each treatment and plateing after serial dilution on NA plates. Mean cfu/seed were determined by averaging the cfu/gm values of three populations in three replicates per treatment after 48 h incubation of the plates at 28° C. Seed for treatments in which mixtures of three isolates were used, were inoculated by using the same total number of bacteria for the inoculum as was used for the single-isolate treatments. Thus, one-third the normal amount of each isolate in the mixture was used.

Trays (35×35 cm.) with 16 (4×4) places per tray (each space was of 7 cm. width, 10 cm. depth and 1 cm. apart from each other) were used, to grow maize. Each place was filled up to 8 cm with non-sterilised soil. Tap water (25 ml.) was added to each hole before planting seeds to adjust the soil to 20% moisture. Four bacterial-treated seeds were added per hole. The experiment in the greenhouse was carried out in four different sets of 16 maize seedlings each, for non-bacterized (control) and bacterized (treated) seeds. In each set, data of 21-days-old seedlings was noted with respect to dry weight of plants. In order for the bacterial strain to be a plant growth promoter, the seedlings treated with the bacteria must have averaged at least 10% higher dry weight than comparable non-bacterized plants.

Of the 150 bacterial strains tested in the greenhouse test, 50 were determined to be plant growth promoting according to the above criteria.

EXAMPLE 4

Screening of Bacterial Strains for Abiotic Stress Tolerance

The bacterial strains that were suppressive to pathogenic fungi in vitro and enhanced plant growth of maize when screened in a greenhouse by growing bacteria-treated maize seeds in non-sterile soil, compared with the control maize plants grown without bacterial treatment, were further screened for abiotic stress tolerance as follows: The stress tolerance of the strains towards salt (NaCl), pH, and temperature was tested by growing them on nutrient broth (NB; Beef extract 5.0 gm, peptone 10.0 gm, sodium chloride 5.0 gm, distilled water 1000 ml, pH 7.2) under various stress conditions, e.g., like 6% salt (NaCl), 5–9 pH, and 55° C. temperature. Viable cells were counted by removing samples at various times in the presence or absence of stress, as indicated. First of all, the 50 strains were subjected to 6% salt stress. Fifteen strains out of 50 were able to grow in the presence of 6% salt stress overnight (14–16 hrs) at 30° C. on a New Brunswick Scientific, USA, Innova Model 4230 refrigerated incubator shaker at 180 rpm. The 15 strains tolerant to 6% salt stress were also able to grow at pH 9.0 stress overnight. However, only 3 strains out of 15 were able to grow at 55° C. stress overnight. Serial dilutions of each sample were spotted (25 µl) onto NA plates, and incubated at 30° C. in triplicate as described earlier [C. S. Nautiyal et al., FEMS Microbiology Letters, Volume 182, pp. 291–296 (2000)]. Viable cells were counted after 2–3 days.

Of the 50 bacterial strains tested in the stress tolerance test, the 3 strains NRRL number *B. lentimorbus* NRRL B-30486, *B. subtilis* NRRL B-30487, and *B. lentimorbus* NRRL B-30488 were thus determined to be stress tolerant according to the above criteria.

EXAMPLE 5

Ability of *B. lentimorbus* NRRL B-30486, *B. subtilis* NRRL B-30487, and *B. lentimorbus* NRRL B-30488 to Solubilize Phosphate under Abiotic Stress Conditions The 3 bacterial strains *B. lentimorbus* NRRL B-30486, *B. subtilis* NRRL B-30487, and *B. lentimorbus* NRRL B-30488 that were suppressive to pathogenic fungi in vitro, enhanced plant growth of maize when screened in a greenhouse by growing bacteria-treated maize seeds in non-sterile soil, compared with the control maize plants grown without bacterial treatment, and were tolerant to abiotic stresses (salt, pH, and temperature), were further screened for their ability to solubilize phosphate under abiotic stress conditions as follows: Quantitative estimation of phosphate solubilization in broth was carried out using Erlenmeyer flasks (150 ml) containing 10 ml of medium inoculated in triplicate with the bacterial strain (100 µl inoculum with approximately $10^9$ cfu/ml).

Value refers to the amount of phosphate solubilized (µg/ml) by strains when individually grown for 3 days in National Botanical Research Institute's phosphate growth medium (NBRIP; glucose, 10 g; $Ca_3(PO_4)_2$ tricalcium phosphate, 5 g; $MgCl_2 \cdot 6H_2O$, 5 g; $MgSO_4 \cdot 7H_2O$, 0.25 g; KCl, 0.2 g and $(NH_4)_2SO_4$, 0.1 g [C. S. Nautiyal, FEMS Microbiology Letters, Volume 170, pp. 265–270 (1999)], at 30° C. in the presence of 0% salt (NaCl) at pH 7. The effect of salt (NaCl), pH, and temperature on solubilization of phosphate was tested by growing them on NBRIP in the presence of NaCl (0, 1, 2, and 4%), pH (7 and 9), and temperature (30 and 45° C.), as indicated (Table 4). Autoclaved, uninoculated batch cultures served as negative controls. Flasks were incubated for 3 days at 30° C. on a New Brunswick Scientific, USA, Innova Model 4230 refrigerated incubator shaker at 180 rpm. The strains were harvested by centrifugation at 10000 rpm for 10 min, using a Sorvall RC 5C centrifuge, Dupont, USA. The concentration of phosphate in culture supernatant was estimated using the Fiske and Subbarow method [C. H. Fiske and Y. Subbarow, Journal of Biological Chemistry, Volume 66, pp. 375–400 (1925)].

TABLE 4

| | | Phosphate solubilisation (µg/ml) | | | |
| | | pH 7 | | pH 9 | |
| % Salt (NaCl) | Strain | 30° C. | 45° C. | 30° C. | 45° C. |
| --- | --- | --- | --- | --- | --- |
| 0 | NRRL B-30486 | 3.0 | 6.6 | 3.8 | 6.1 |
| 1 | | 4.7 | 6.5 | 4.6 | 11.6 |
| 2 | | 4.5 | 9.9 | 4.8 | 11.2 |
| 4 | | 4.8 | 10.5 | 4.1 | 10.3 |
| 0 | NRRL B-30487 | 2.4 | 1.3 | 0.83 | 1.5 |
| 1 | | 3.4 | 6.0 | 2.8 | 3.2 |
| 2 | | 6.2 | 6.0 | 5.5 | 5.7 |
| 4 | | 2.5 | 12.5 | 5.6 | 13.2 |
| 0 | NRRL B-30488 | 33.8 | 42.9 | 42.9 | 43.0 |
| 1 | | 17.0 | 42.9 | 13.5 | 43.0 |
| 2 | | 12.0 | 0.0 | 19.4 | 43.0 |
| 4 | | 13.0 | 0.0 | 8.8 | 43.0 |

All three of the bacterial strains *B. lentimorbus* NRRL B-30486, *B. subtilis* NRRL B-30487, and *B. lentimorbus* NRRL B-30488 demonstrated variable phosphate solubilization induction ability, under in vitro conditions in the presence of high salt, high pH, and high temperature stress.

EXAMPLE 6

Ability of *B. lentimorbus* NRRL B-30486, *B. subtilis* NRRL B-30487, and *B. lentimorbus* NRRL B-30488 Under In Vitro Conditions to Suppress Pathogenic Fungi in the Presence or Absence of High Salt and pH Stress The three bacterial strains *B. lentimorbus* NRRL B-30486, *B. subtilis* NRRL B-30487, and *B. lentimorbus* NRRL B-30488 were screened for their biocontrol activity against several plant pathogenic fungi, under in vitro conditions in the presence or absence of high salt and pH stress (Table 5).

TABLE 5

| Pathogenic | Inhibition zone (mm) | | |
|---|---|---|---|
| strain | B-30486 | B-30487 | B-30488 |
| *Fusarium oxysporum* f. sp. *ciceri* | | | |
| pH 3; 0% salt (NaCl) | 10 | 20 | 10 |
| pH 3; 2% salt | 20 | 25 | 20 |
| pH 3; 4% salt | 10 | NG* | 20 |
| pH 7; 0% salt | 8 | 6 | 7 |
| pH 7; 2% salt | 17 | 20 | 15 |
| pH 7; 4% salt | 12 | NG | 16 |
| pH 9; 0% salt | 5 | 5 | 5 |
| pH 9; 2% salt | 20 | 10 | 15 |
| pH 9; 4% salt | 13 | NG | 14 |
| pH 11; 0% salt | 15 | 10 | 20 |
| pH 11; 2% salt | 20 | 20 | 20 |
| pH 11; 4% salt | 15 | 10 | 20 |
| *Sclerotium rolfsii* | | | |
| pH 3; 0% salt (NaCl) | 5 | NZ** | 5 |
| pH 3; 2% salt | 10 | 5 | NZ |
| pH 3; 4% salt | 20 | 5 | NG |
| pH 7; 0% salt | 3 | 10 | NZ |
| pH 7; 2% salt | 4 | 3 | 2 |
| pH 7; 4% salt | NG | NG | NG |
| pH 9; 0% salt | 8 | NZ | 7 |
| pH 9; 2% salt | 13 | 7 | 13 |
| pH 9; 4% salt | 25 | 10 | 20 |
| pH 11; 0% salt | 5 | NZ | NZ |
| pH 11; 2% salt | 20 | 20 | 20 |
| pH 11; 4% salt | 20 | 5 | 25 |
| Inhibition zone at pH 7; 0% salt | | | |
| *Rhizoctonia solani* | 6 | NZ | 3 |
| *Alternaria solani* | 10 | 6 | 8 |
| *Pythium aphanidermatum* | 10 | 4 | 10 |
| *Phytophthora palmivora* | 6 | 12 | 7 |
| *Sclerotinia sclerotiorum* | 14 | 10 | 11 |
| *Colletotrichum falcatum* | 11 | 10 | NZ |
| Penicillium sp. | 2 | 5 | NZ |
| *Curvularia lunata* | 2 | 3 | 10 |
| *Aspergillus niger* | 2 | 10 | 3 |
| *Phoma sorghii* | NZ | 5 | NZ |
| *Fusarium moniliforme* | 11 | 6 | 10 |

NG* = No growth of fungi;
NZ** = No inhibition zone

All three of the bacterial strains *B. lentimorbus* NRRL B-30486, *B. subtilis* NRRL B-30487, and *B. lentimorbus* NRRL B-30488 demonstrated variable biocontrol activity against several phytopathogenic fungi, under in vitro conditions in the presence of high salt and/or pH stress. The strains also demonstrated variable biocontrol activity activity against several phytopathogenic fungi, under in vitro conditions in the presence or absence of high salt and pH stress. Therefore, the possibility of using consortium of all the three bacteria was explored.

EXAMPLE 7

Interaction of *B. lentimorbus* NRRL B-30486, *B. subtilis* NRRL B-30487, and *B. lentimorbus* NRRL B-30488 Individually and Their Consortium, Under In Vitro Conditions with Chickpea Phytopathogenic Fungi Interaction of *F. oxysporum* f. sp. *ciceri, Rhizoctonia solani, Pythium* sp., and *S. sclerotiorum* with *B. lentimorbus* NRRL B-30486, *B. subtilis* NRRL B-30487, and *B. lentimorbus* NRRL B-30488 individually and in a consortium in liquid medium was elucidated in a dual culture test by growing the bacterium/consortium on nutrient broth in the presence and absence of the fungi. An agar disk (5-mm in diameter) of the *F. oxysporum* f. sp. *ciceri, Rhizoctonia solani, Pythium* sp., and *S. sclerotiorum* was individually inoculated in 150-ml Erlenmeyer flasks containing 50 ml nutrient broth.

A suspension of *B. lentimorbus* NRRL B-30486, *B. subtilis* NRRL B-30487, and *B. lentimorbus* NRRL B-30488 individually and its consortium, containing $10^8$ cfu/ml was inoculated and the flasks were incubated at 30° C. for 7 days in an incubator shaker under static condition, and the control cultures were grown without bacteria. A consortium of the three bacterial strains *B. lentimorbus* NRRL B-30486, *B. subtilis* NRRL B-30487, and *B. lentimorbus* NRRL B-30488 was prepared by mixing three cultures of approximately $10^8$ cfu/ml, in the ratio of 1:1:1. Mycelial dry weight of the fungus grown in the presence and absence of *B. lentimorbus* NRRL B-30486, *B. subtilis* NRRL B-30487, and *B. lentimorbus* NRRL B-30488 individually and its consortium was determined by filtering out the spent media using a Whatman filter paper no. 1, and drying the fungal mass on the filter paper at 60° C. for 3 days. Test results of the interaction of *B. lentimorbus* NRRL B-30486, *B. subtilis* NRRL B-30487, and *B. lentimorbus* NRRL B-30488 individually and in a consortium, under in vitro conditions with *F. oxysporum* f. sp. *ciceri, Rhizoctonia solani, Pythium* sp., and *S. sclerotiorum* are presented in Table 6.

TABLE 6

| | Fungus | |
|---|---|---|
| Treatment | Dry weight (mg) | % inhibition over control |
| *Fusarium oxysporum* f. sp. *ciceri*(FO) | | |
| 1. FO | 150 | 0 |
| 2. FO + B-30486 | 78 | 48 |
| 3. FO + B-30487 | 96 | 36 |
| 4. FO + B-30488 | 84 | 44 |
| 5. FO + B-30486 + B-30487 + B-30488 | 56 | 63 |
| *Rhizoctonia solani* (RS) | | |
| 1. RS | 80 | 0 |
| 2. RS + B-30486 | 30 | 63 |
| 3. RS + B-30487 | 34 | 58 |
| 4. RS + B-30488 | 48 | 40 |
| 5. RS + B-30486 + B-30487 + B-30488 | 26 | 68 |
| Pythium sp. (PS) | | |
| 1. PS | 50 | 0 |
| 2. PS + B-30486 | 40 | 20 |
| 3. PS + B-30487 | 48 | 4 |
| 4. PS + B-30488 | 23 | 54 |
| 5. PS + B-30486 + B-30487 + B-30488 | 21 | 58 |

TABLE 6-continued

| Treatment | Fungus | |
|---|---|---|
| | Dry weight (mg) | % inhibition over control |
| *Sclerotinia sclerotiorum* (SS) | | |
| 1. SS | 313 | 0 |
| 2. SS + B-30486 | 72 | 77 |
| 3. SS + B-30487 | 96 | 69 |
| 4. SS + B-30488 | 84 | 73 |
| 5. SS + B-30486 + B-30487 + B-30488 | 64 | 80 |

As can be seen from the results which are presented in Table 6, all the three bacterial strains *B. lentimorbus* NRRL B-30486, *B. subtilis* NRRL B-30487, and *B. lentimorbus* NRRL B-30488 individually and their consortium effectively inhibited the growth of *F. oxysporum* f. sp. *ciceri*, *Rhizoctonia solani*, *Pythium* sp., and *S. sclerotiorum* under in vitro conditions. However, the consortium of the bacterial strains was most effective in inhibiting the growth of the test fungi.

EXAMPLE 8

Survival of *B. lentimorbus* NRRL B-30486, *B. subtilis* NRRL B-30487, and *B. lentimorbus* NRRL B-30488 Individually and in a Consortium, on Vermiculite as Carrier Determination of the survival of the bacterial strains *B. lentimorbus* NRRL B-30486, *B. subtilis* NRRL B-30487, and *B. lentimorbus* NRRL B-30488 individually and in a consortium, on vermiculite as carrier, over the period of twelve months, at 10° C. was accomplished according to following method. The three bacterial strains *B. lentimorbus* NRRL B-30486, *B. subtilis* NRRL B-30487, and *B. lentimorbus* NRRL B-30488 were grown individually in liquid growth medium NB. Cultures were grown in 2-liter flasks containing 1.5 liters of NB medium and incubated for 2 days at 30° C. on a New Brunswick Scientific, USA, Innova Model 4230 refrigerated incubator shaker at 180 rpm. After 2 days of growth 300 ml of the culture was added to an autoclavable plastic bag containing 1 kg of sterile vermiculite, which yielded approximately 30% moisture of the product. A consortium of the three bacterial strains *B. lentimorbus* NRRL B-30486, *B. subtilis* NRRL B-30487, and *B. lentimorbus* NRRL B-30488 was prepared by mixing three cultures of approximately $10^{8.5}$ cfu/ml, in the ratio of 1:1:1. The sealed bags were incubated for 2 days at 30° C. to cure the bioinoculant preparation. After curing, the sealed bags were stored at 10° C. and aliquots were periodically removed for viability measurements (Table 7). Viability of the product was determined by standard serial dilution method on NA plates.

TABLE 7

| | Log cfu/g of vermiculite | | | |
|---|---|---|---|---|
| Months | B-30486 | B-30487 | B-30488 | B-30486 + B-30487 + B-30487 (Consortium) |
| 0 | 8.4 | 8.8 | 8.4 | 8.5 |
| 1 | 10.2 | 9.7 | 10.3 | 9.8 |
| 2 | 9.8 | 9.7 | 9.9 | 9.2 |
| 4 | 9.4 | 9.3 | 9.6 | 9.2 |
| 6 | 8.8 | 8.3 | 8.9 | 8.8 |
| 9 | 8.4 | 8.3 | 8.5 | 8.8 |
| 12 | 7.9 | 7.7 | 8.3 | 8.1 |

As shown in the Table 7, all the three strains *B. lentimorbus* NRRL B-30486, *B. subtilis* NRRL B-30487, and *B. lentimorbus* NRRL B-30488 individually and in a consortium demonstrated good survival rates during long-term storage in vermiculite at 10° C. After twelve months of storage, approximately $10^8$ cfu/g of vermiculite wwere present. These data indicate that vermiculite works as an excellent carrier material for the strains to be later inoculated onto seeds, plants or soil, as no appreciable loss of cell viability was observed.

EXAMPLE 9

Biocontrol Activity of *B. lentimorbus* NRRL B-30486, *B. subtilis* NRRL B-30487, and *B. lentimorbus* NRRL B-30488 Individually and in a Consortium, in Greenhouse Against Chickpea Phytopathogenic Fungi The three bacterial strains *B. lentimorbus* NRRL B-30486, *B. subtilis* NRRL B-30487, and *B. lentimorbus* NRRL B-30488 were screened individually and in a consortium, in greenhouse against chickpea phytopathogenic fungi. Cultivation of fungi for plant assay was accomplished using a 1000 ml-Eelenmeyer flask with 100 g corn and 400 g coarse sand. The flask was autoclaved and after autoclaving moisture was adjusted to 15% with sterile distilled water. The flask was incubated at 30° C. individually with one 10 mm diameter agar plug from a nutrient agar culture of *F. oxysporum* f. sp. *ciceri*, *R. solani* and *Pythium* sp. in the dark for 4 weeks. After four weeks the mixture was air-dried and ground and sieved to obtain particles 0.5 mm in size. Each of the inocula was intimately mixed with sterile soil at 0.15% inoculum per total weight of soil, to give a final mixture of 0.45% inoculum of *F. oxysporum* f. sp. *ciceri*, *R. solani* and *Pythium* sp. per total weight of soil as described earlier [C. S. Nautiyal, Current Microbiology, Volume 35, pp. 52–58 (1997)].

The experiment to examine the biocontrol activity of *B. lentimorbus* NRRL B-30486, *B. subtilis* NRRL B-30487, and *B. lentimorbus* NRRL B-30488 individually and in a consortium was carried out in four different sets of 30 chickpea seedlings each, for treated and non-treated seeds (control). Chickpea seeds were prepared for inocula of *B. lentimorbus* NRRL B-30486, *B. subtilis* NRRL B-30487, and *B. lentimorbus* NRRL B-30488 individually and in a consortium, prepared as described in Example 3, except vermiculite was used as carrier as described in Example 8, instead of direct inoculum from petri plate. In each set, data were noted during five months of plant growth with respect to seedling germination, seedling mortality (dead seedlings, stunting of shoot height, drooping of leaves, root decolourisation), plant height, number of pods and seed dry weight. The results are tabulated in the following Table 8.

TABLE 8

| Observations | Inoculum | Treatment | | % increase over control |
|---|---|---|---|---|
| | | Un-inoculated control | Inoculated | |
| Seedling germination (%) | B-30486 | 82 | 93 | 13.41 |
| Seedling mortality (%) | | 87 | 31 | −64.36 |
| Plant height (cm) | | 29 | 37 | 27.58 |
| Number of pods/plant | | 39 | 48 | 23.07 |
| Seed dry weight/ 100 seeds (g) | | 17 | 20 | 18.78 |
| Seedling germination (%) | B-30487 | 71 | 82 | 15.49 |
| Seedling mortality (%) | | 87 | 38 | −56.32 |
| Plant height (cm) | | 29 | 34 | 17.24 |
| Number of pods/plant | | 39 | 43 | 10.25 |
| Seed dry weight/ 100 seeds (g) | | 17 | 19 | 12.73 |
| Seedling germination (%) | B-30488 | 82 | 100 | 21.95 |
| Seedling mortality (%) | | 87 | 28 | −67.8 |
| Plant height (cm) | | 29 | 41 | 41.37 |
| Number of pods/plant | | 39 | 52 | 33.33 |
| Seed dry weight/ 100 seeds (g) | | 17 | 20 | 21.95 |
| Seedling germination (%) | B-30486 + B-30487 + B-30488 (Consortium) | 82 | 100 | 21.95 |
| Seedling mortality (%) | | 87 | 10 | −88.5 |
| Plant height (cm) | | 29 | 43 | 48.27 |
| Number of pods/plant | | 39 | 61 | 56.41 |
| Seed dry weight/ 100 seeds (g) | | 17 | 23 | 39.5 |

As can be seen from the results which are presented in Table 8, inoculated plants demonstrated less seedling mortality, and better seedling germination, plant height, number of pods and seed dry weight, compared with un-inoculated control. Among the inoculated plants, the consortium showed the best results in terms of less seedling mortality, and better seedling germination, plant height, number of pods and seed dry weight.

EXAMPLE 10

Plant Growth Promotion Activity of *B. lentimorbus* NRRL B-30486, *B. subtilis* NRRL B-30487, and *B. lentimorbus* NRRL B-30488, Individually and in a Consortium, in Greenhouse Using Chickpea The experiment to examine the plant growth promotion activity of *B. lentimorbus* NRRL B-30486, *B. subtilis* NRRL B-30487, and *B. lentimorbus* NRRL B-30488 individually and in a consortium was carried out in four different sets of 30 chickpea seedlings each, for treated and non-treated seeds (control). Chickpea seeds were prepared for inocula of *B. lentimorbus* NRRL B-30486, *B. subtilis* NRRL B-30487, and *B. lentimorbus* NRRL B-30488 individually and in a consortium using vermiculite as carrier as described in Example 9. In each set, data were noted during five months of plant growth with respect to seedling germination, plant height, number of pods and seed dry weight. The results are tabulated in the following Table 9.

TABLE 9

| Observations | | Treatment | | |
|---|---|---|---|---|
| | | Un-inoculated control | Inoculated | % increase over control |
| Seedling germination (%) | B-30486 | 82 | 100 | 21.95 |
| Plant height (cm) | | 29 | 38 | 31.03 |
| Number of pods/plant | | 39 | 53 | 35.89 |
| Seed dry weight/ 100 seeds (g) | | 17 | 21 | 27.88 |
| Seedling germination (%) | B-30487 | 82 | 92 | 12.19 |
| Plant height (cm) | | 29 | 39 | 34.48 |
| Number of pods/plant | | 39 | 46 | 17.95 |
| Seed dry weight/ 100 seeds (g) | | 17 | 20 | 18.78 |
| Seedling germination (%) | B-30488 | 82 | 100 | 21.95 |
| Plant height (cm) | | 29 | 44 | 51.72 |
| Number of pods/plant | | 39 | 59 | 51.28 |
| Seed dry weight/ 100 seeds (g) | | 17 | 23 | 40.0 |

TABLE 9-continued

|  | | Treatment | | |
| --- | --- | --- | --- | --- |
| Observations | | Un-inoculated control | Inoculated | % increase over control |
| Seedling germination (%) | B-30486 + B-30487 + B-30488 (Consortium) | 82 | 100 | 21.95 |
| Plant height (cm) | | 29 | 46 | 58.62 |
| Number of pods/plant | | 39 | 64 | 64.10 |
| Seed dry weight/ 100 seeds (g) | | 17 | 25 | 48.48 |

As can be seen from the results which are presented in Table 9, inoculated plants demonstrated better seedling germination, plant height, number of pods and seed dry weight, compared with un-inoculated control. Among the inoculated plants, the consortium showed best results in terms of better seedling germination, plant height, number of pods and seed dry weight.

EXAMPLE 11

Plant Growth Promotion Activity of the Consortium of *B. lentimorbus* NRRL B-30486, *B. subtilis* NRRL B-30487, and *B. lentimorbus* NRRL B-30488 in Greenhouse on Various Plants Seeds were prepared and inoculated to test the plant growth promotion activity of the consortium of *B. lentimorbus* NRRL B-30486, *B. subtilis* NRRL B-30487, and *B. lentimorbus* NRRL B-30488 in greenhouse on various plants, as described above in example 8. The experiment in a greenhouse was carried out in four different sets of 16 seedlings each, for non-bacterized (control) and bacterized (treated) seeds of *Zea mays, Abelmoschus esculentus, Luffa cylindrica, Lycopersicon esculentum*, and *Cucumis sativus*. In each set, data of 21-days-old seedlings were noted with respect to dry weight of plants. The results of the plant growth promotion activity of the consortium of *B. lentimorbus* NRRL B-30486, *B. subtilis* NRRL B-30487, and *B. lentimorbus* NRRL B-30488 in a greenhouse on various plants are given in Table 10.

TABLE 10

| Test plants | Dry weight (mg)/plant | | |
|---|---|---|---|
| | Un-inoculated control | Inoculated | % increase over control |
| 1. *Zea mays* | 67.5 | 80 | 18.51 |
| 2. *Abelmoschus esculentus* | 20 | 35 | 75.0 |
| 3. *Luffa cylindrica* | 76 | 110 | 44.73 |
| 4. *Lycopersicon esculentum* | 2 | 5 | 150.0 |
| 5. *Cucumis sativus* | 25 | 110 | 340.0 |

As the data in Table 10 demonstrate, variable plant growth promoting response on the dry weight of *Zea mays, Abelmoschus esculentus, Luffa cylindrica, Lycopersicon esculentum*, and *Cucumis sativus* by the consortium of *B. lentimorbus* NRRL B-30486, *B. subtilis* NRRL B-30487, and *B. lentimorbus* NRRL B-30488 in the greenhouse is observed. As can be seen from the results, the dry weight of the bacterized seedlings was higher in the range of 18–340% compared with non-bacterized seedlings.

EXAMPLE 12

Field Trial of Biocontrol Activity of the Consortium of *B. lentimorbus* NRRL B-30486, *B. subtilis* NRRL B-30487, and *B. lentimorbus* NRRL B-30488 Against Chickpea Phytopathogenic Fungi Biocontrol activity of the consortium of *B. lentimorbus* NRRL B-30486, *B. subtilis* NRRL B-30487, and *B. lentimorbus* NRRL B-30488 against chickpea phytopathogenic fungi was field tested on the farms of Banaras Hindu University, Varanasi; Chandra Shekhar Azad University of Agriculture & Technology, Kanpur, and Indian Agricultural Research Institute, New Delhi on plots with a consistent history of heavy infection of chickpea variety Radhey, by *F. oxysporum* f. sp. *ciceri*. The bacterial strains were propagated as described in Example 8. All the trials were seeded in October, 2000 and harvested after five months of growth in March, 2001. Field soil moisture at the time of seeding was in the range of 25–30% and the crop was entirely rain fed. Mechanical cultivation practices were not used after seeding. Each experiment was in a randomized block design. Six replicates per treatment within blocks consisted of plots of three 4-m rows (30 cm spacing). After 10 days of germination, seedlings were thinned out to 50 seedlings per row. All results were collected from the middle rows, excluding two adjacent rows as guard rows, for both non-bacterized (control) and bacterized (treated) seeds of chickpea with consortium of *B. lentimorbus* NRRL B-30486, *B. subtilis* NRRL B-30487, and *B. lentimorbus* NRRL B-30488 (Log 8 Cfu/ml). Values are the mean of six replications of 10 plants each, whereas values for the dry weights (g) are the mean of 100 seeds chosen at random from six replications of 10 plants each.

TABLE 11

| Observations | Location | Treatment | | % increase over control |
|---|---|---|---|---|
| | | Un-inoculated control | Inoculated | |
| Seedling survival (%) | Varanasi | 55 | 73 | 33.69 |
| Plant height (cm) | | 41 | 57 | 38.05 |
| Number of pods/plant | | 65 | 79 | 20.39 |
| Weight of 100 seeds (g) | | 17 | 20 | 19.87 |
| Yield/plot (g) | | 410 | 725 | 76.83 |
| Seedling survival (%) | Kanpur | 40 | 83 | 105.19 |
| Plant height (cm) | | 47 | 62 | 32.2 |
| Number of pods/plant | | 62 | 94 | 51.61 |
| Weight of 100 seeds (g) | | 16 | 20 | 24.68 |
| Yield/plot (g) | | 345 | 870 | 152.17 |
| Seedling survival (%) | New Delhi | 47 | 87 | 85.11 |
| Plant height (cm) | | 47 | 57 | 21.27 |
| Number of pods/plant | | 44 | 104 | 136.36 |
| Weight of 100 seeds (g) | | 15 | 19 | 26.49 |
| Yield/plot (g) | | 450 | 900 | 100.0 |

As can be seen from the data in Table 11, at all the three locations compared to control, chickpea seeds treated with consortium of *B. lentimorbus* NRRL B-30486, *B. subtilis* NRRL B-30487, and *B. lentimorbus* NRRL B-30488 improved plant performance, in terms of enhanced % seedling survival, plant height, number of pods/plant, weight of 100 seeds, and yield/plot.

EXAMPLE 13

Survival of *B. lentimorbus* NRRL B-30486, *B. subtilis* NRRL B-30487, and *B. lentimorbus* NRRL B-30488 Individually and in a Consortium, on Charcoal as Carrier Determination of the survival of 3 bacterial strains *B. lentimorbus* NRRL B-30486, *B. subtilis* NRRL B-30487, and *B. lentimorbus* NRRL B-30488 individually and in a consortium, on charcoal as carrier, over the period of six months, at 10° C. was accomplished according to following method. The three bacterial strains *B. lentimorbus* NRRL B-30486, *B. subtilis* NRRL B-30487, and *B. lentimorbus* NRRL B-30488 were grown individually in liquid growth medium NB. Cultures were grown in 2-liter flasks containing 1.5 liters of NB medium and incubated for 2 days at 30° C. on a New Brunswick Scientific, USA, Innova Model 4230 refrigerated incubator shaker at 180 rpm. After 2 days of growth 600 ml of the culture was added to an autoclavable plastic bag containing 1 kg of sterile charcoal, which yielded approximately 30% moisture of the product. A consortium of the three bacterial strains *B. lentimorbus* NRRL B-30486, *B. subtilis* NRRL B-30487, and *B. lentimorbus* NRRL B-30488 was prepared by mixing three cultures of approximately $10^{8.5}$ cfu/ml, in the ratio of 1:1:1. The bioinoculant preparation was cured by incubating the sealed bags for 2 days at 30° C. After curing, the sealed bags were stored at 10° C. and aliquots were periodically removed for viability measurements. Viability of the product was determined by standard serial dilution method on NA plates.

Table 12 shows the survival of three bacterial strains *B. lentimorbus* NRRL B-30486, *B. subtilis* NRRL B-30487, and *B. lentimorbus* NRRL B-30488 individually and in a consortium, on charcoal as carrier, over the period of six months, at 10° C., following harvesting.

TABLE 12

| Months | Log cfu/g on charcoal | | | |
|---|---|---|---|---|
| | B-30486 | B-30487 | B-30488 | B-30486 + B-30487 + B-30487 (Consortium) |
| 0 | 8.4 | 8.8 | 8.4 | 8.5 |
| 1 | 9.2 | 9.5 | 9.6 | 9.2 |
| 2 | 9.1 | 9.1 | 9.5 | 9.6 |
| 4 | 8.7 | 8.4 | 8.9 | 8.7 |
| 6 | 7.1 | 7.6 | 7.5 | 7.8 |

As shown in the Table 12, all the three strains *B. lentimorbus* NRRL B-30486, *B. subtilis* NRRL B-30487, and *B. lentimorbus* NRRL B-30488 individually and in a consortium demonstrated good survival rates during long-term storage in charcoal at 10° C. After six months of storage, approximately $10^7$ cfu/g was present. These data indicate that charcoal works as an excellent carrier material, albeit not as effective when compared with vermiculite, for the strains to be later inoculated onto seeds, plants or soil. However, as a carrier material the cost of charcoal is 8-fold less, compared with vermiculite. Therefore, the lower cost of the charcoal makes its choice as a carrier very attractive for its large-scale commercial use.

EXAMPLE 14

Use of Sugar Factory Sulphitation Press Mud and Distillery Spent Wash as Carrier for Preparing at Commercial Scale Consortium of *B. lentimorbus* NRRL B-30486, *B. subtilis* NRRL B-30487, and *B. lentimorbus* NRRL B-30488

The following procedures were performed to utilize sugar factory sulphitation press mud and distillery spent wash as carrier for preparing at commercial scale, after its fermentation-using consortium of *B. lentimorbus* NRRL B-30486, *B. subtilis* NRRL B-30487, and *B. lentimorbus* NRRL B-30488.

Cultures of *B. lentimorbus* NRRL B-30486, *B. subtilis* NRRL B-30487, and *B. lentimorbus* NRRL B-30488 were grown individually in molasses diluted with water in the ratio of 1:5. Cultures were grown in 2-liter flasks containing 1.5 liters of molasses diluted with water in the ratio of 1:5 and incubated for 3 days at 30° C. on a New Brunswick Scientific, USA, Innova Model 4230 refrigerated incubator shaker at 180 rpm. After 3 days of growth a consortium of the three bacterial strains B. lentimorbus NRRL B-30486, B. subtilis NRRL B-30487, and B. lentimorbus NRRL B-30488 was prepared by mixing the three cultures of approximately $10^9$ cfu/ml, in the ratio of 1:1:1. The consortium of the three bacterial strains thus obtained was further diluted with water in the ratio of 1:10, containing approximately $10^8$ to $10^9$ cfu/ml. Growing the bacteria in molasses makes the process economically very viable.

About 300 tons of fresh sulphinated press mud, obtained while clarifying sugarcane juice with lime and sulphur dioxide, is laid out on a cement floor with width of 2.5 meter, 1.5 meter tall, and length of 150 meter windrows. The press mud was churned and homogenized, either manually or by the help of an aero tiller, before adding about 600 liters of a consortium of *B. lentimorbus* NRRL B-30486, *B. subtilis* NRRL B-30487, and *B. lentimorbus* NRRL B-30488, prepared as described above, i.e., 2 liter of the consortium/ton of press mud and mixing again. Within 2–3 days, the temperature of the windrows goes up to 70–75° C. Thereafter, the windrows are churned twice a day and spent wash is sprayed on daily basis to maintain 55–65% moisture, for up to 40 days. After about 40 sprays the spraying of spent wash is stopped and the windrows are regularly turned for 3–5 days to reduce the moisture of the fermented product to about 30%. Usually after 45 days, the temperature of the windrows goes down to 40–45° C. The product at this stage is totally fermented and ready for its application and packaging.

To monitor the presence of *Bacillus* strains during the fermentation process of the windrows, spontaneous rifampicin-resistant ($Rif^r$) strain derivative of *B. lentimorbus* NRRL B-30488 was isolated on NA plates, containing 100 μg rifampicin. A spontaneous *B. lentimorbus* NRRL B-30488R $Rif^r$ strain showing growth comparable to the wild type *B. lentimorbus* NRRL B-30488 based on the size of colony, on agar plates containing 100 μg rifampicin, was selected for further studies. Agar plates containing 100 μg rifampicin/ml, an amount sufficient to inhibit the growth of other bacteria in non-sterilized press mud and spent wash were used to recover *B. lentimorbus* NRRL B-30488R from the windrows during the fermentation process. Presence of *B. lentimorbus* NRRL B-30488R $10^8$ cfu/gm in the fermented product by 45 days is indicative of the survival, multiplication and continued presence of the *B. lentimorbus* NRRL B-30488R, during the fermentation process.

EXAMPLE 15

Use of Sugar Factory Carbonation Press Mud as Carrier for Preparing at Commercial Scale Consortium of *B. lentimorbus* NRRL B-30486, *B. subtilis* NRRL B-30487, and *B. lentimorbus* NRRL B-30488

The procedures for fermenting sugar factory carbonation press mud as carrier for preparing at commercial scale, using a consortium of *B. lentimorbus* NRRL B-30486, *B. subtilis* NRRL B-30487, and *B. lentimorbus* NRRL B-30488, were same as described as above in example 14, except water was used instead of spent wash to maintain the moisture during fermentation.

EXAMPLE 16

Comparative Analysis of Plant Growth Promotion Activity of the Consortium of *B. lentimorbus* NRRL B-30486, *B. subtilis* NRRL B-30487, and *B. lentimorbus* NRRL B-30488 in Greenhouse Using Vermiculite, Charcoal, Fermented Sugar Factory Sulphitation Press Mud and Distillery Spent Wash, and Sugar Factory Carbonation Press Mud as Carrier, on Plants Seeds were prepared and inoculated with the consortium of *B. lentimorbus* NRRL B-30486, *B. subtilis* NRRL B-30487, and *B. lentimorbus* NRRL B-30488 in a greenhouse using vermiculite, charcoal, fermented sugar factory sulphitation press mud and distillery spent wash, and sugar factory carbonation press mud as carriers to test the plant growth promotion activity of the consortium of *B. lentimorbus* NRRL B-30486, *B. subtilis* NRRL B-30487, and *B. lentimorbus* NRRL B-30488 in the greenhouse on various plants, as described above in Examples 8, 13, 14, and 15, respectively. The experiment in greenhouse was carried out in four different sets of 16 seedlings each, for non-bacterized (control) and bacterized (treated) seeds of *A. esculentus, C. sativus, Z. mays, Triticum aestivum, Glycine max, Pisum sativum*, and *Impatiens balsamina*. In each set, data of 21-days-old seedlings were noted with respect to dry weight of plants. The results of the plant growth promotion activity of the consortium of *B. lentimorbus* NRRL B-30486, *B. subtilis* NRRL B-30487, and *B. lentimorbus* NRRL B-30488 in the greenhouse on various plants, while using vermiculite, charcoal, fermented sugar factory sulphitation press mud and distillery spent wash, and sugar factory carbonation press mud as carriers, are given in Table 13.

TABLE 13

| | | Dry weight (mg)/plant | | |
|---|---|---|---|---|
| Plant | Carrier | Un-inoculated control | Inoculated | % increase over control |
| 1. *A. esculentus* | Vermiculite | 28 | 47 | 67.85 |
| 2. *C. sativus* | | 30 | 95 | 216.67 |
| 3. *Z. mays* | | 61 | 74 | 21.31 |
| 4. *Triticum aestivum* | | 15 | 23 | 53.33 |
| 5. *Glycine max* | | 47 | 73 | 55.32 |
| 6. *Pisum sativum* | | 57 | 85 | 49.12 |
| 7. *Impatiens balsamina* | | 4 | 12 | 200.0 |
| 1. *A. esculentus* | Charcoal | 31 | 50 | 61.23 |
| 2. *C. sativus* | | 34 | 94 | 176.4 |
| 3. *Z. mays* | | 65 | 83 | 27.63 |
| 4. *Triticum aestivum* | | 17 | 26 | 52.94 |
| 5. *Glycine max* | | 42 | 72 | 71.42 |

TABLE 13-continued

| | | Dry weight (mg)/plant | | |
|---|---|---|---|---|
| Plant | Carrier | Un-inoculated control | Inoculated | % increase over control |
| 6. *Pisum sativum* | | 52 | 83 | 59.62 |
| 7. *Impatiens balsamina* | | 4 | 9 | 125.0 |
| 1. *A. esculentus* | Fermented sugar factory sulphitation press mud and distillery spent wash | 25 | 38 | 52.0 |
| 2. *C. sativus* | | 28 | 56 | 100.0 |
| 3. *Z. mays* | | 57 | 70 | 22.81 |
| 4. *Triticum aestivum* | | 13 | 20 | 53.84 |
| 5. *Glycine max* | | 40 | 69 | 72.5 |
| 6. *Pisum sativum* | | 49 | 76 | 55.1 |
| 7. *Impatiens balsamina* | | 5 | 10 | 100.0 |
| 1. *A. esculentus* | Fermented sugar factory carbonation press mud | 36 | 54 | 50.0 |
| 2. *C. sativus* | | 33 | 63 | 90.90 |
| 3. *Z. mays* | | 52 | 66 | 26.92 |
| 4. *Triticum aestivum* | | 12 | 20 | 66.62 |
| 5. *Glycine max* | | 42 | 71 | 69.05 |
| 6. *Pisum sativum* | | 48 | 74 | 54.17 |
| 7. *Impatiens balsamina* | | 4 | 10 | 150.0 |

As the data in Table 13 demonstrate, variable plant growth promoting response on the dry weight of different plants by the consortium of *B. lentimorbus* NRRL B-30486, *B. subtilis* NRRL B-30487, and *B. lentimorbus* NRRL B-30488 is observed in the greenhouse. As can be seen from the results, the dry weight of the bacterised seedlings of *A. esculentus, C. sativus, Z. mays, Triticum aestivum, Glycine max, Pisum sativum*, and *Impatiens balsamina* was higher in the range of 21–150% compared with non-bacterized seedlings, using vermiculite, charcoal, fermented sugar factory sulphitation press mud and distillery spent wash, and sugar factory carbonation press mud as carriers.

EXAMPLE 17

Field Trial of Biocontrol Activity of the Consortium of *B. lentimorbus* NRRL B-30486, *B. subtilis* NRRL B-30487, and *B. lentimorbus* NRRL B-30488 Against Sugarcane Phytopathogenic Fungi, Using Vermiculite as Carrier Field trial plot size for all the field trials was of 9.0×3.5 meter plot size, consisting of four rows for each treatment, in triplicate.

Field trials using sugarcane variety Cos 95255 were conducted by placing sugarcane sets at the time of sowing directly on vermiculite containing the consortium of *B. lentimorbus* NRRL B-30486, *B. subtilis* NRRL B-30487, and *B. lentimorbus* NRRL B-30488, to the saturation of 20%.

Inoculum of both the pathogens *Fusarium moniliforme* and *Colletotrichum falcatum* multiplied in liquid medium was prepared for a dual culture test by growing the fungi individually on NB. An agar disk (5-mm in diameter) of the *F. moniliforme* and *C. falcatum* were individually inoculated into 250-ml Erlenmeyer flasks containing 100 ml NB. The flasks were incubated at 30° C. for 10 days under static condition. The inoculum was diluted with sterile 0.85% saline Milli Q water (MQW) to a spore concentration of $10^5$ to $10^6$ spores/ml. Sets were dipped in the inoculum thus prepared of *F. moniliforme* or *C. falcatum* as indicated for 30 minutes before planting. The inoculum was also used to drench the rows before planting sugarcane. Also the experiment was conducted in a wilt sick plot where in previous year wilt incidence was as high as 95%.

The first sugarcane trial was conducted using pots (9 inches diameter) in August, 2000, at Dhampur Sugar Mills Ltd., Rozagaon, Faizabad using the consortium. After three months of growth plants from pots were shifted into field. The number of infected plants, plant height, number of tillers, and girth of cane were noted in August, 2001. The test results are given in Table 14.

TABLE 14

| Observations | Fungus | Treatment Un-inoculated control | Inoculated | % increase over control |
|---|---|---|---|---|
| Mortality (%) | *Fusarium moniliforme* | 30 | 0 | n.a.* |
| Plant height (cm) | | 161.8 | 181.4 | 12.11 |
| Number of tillers/plant | | 3.1 | 6.4 | 106.4 |
| Girth of cane (cm) | | 5.8 | 8.1 | 39.66 |
| Mortality (%) | *Colletotrichum falcatum* | 80 | 0 | n.a. |
| Plant height (cm) | | 152 | 162 | 6.57 |
| Number of tillers/plant | | 4.6 | 6.6 | 43.47 |
| Girth of cane (cm) | | 5.8 | 7.8 | 34.48 |

*n.a. = Not applicable

The results presented in Table 14 clearly demonstrate effective biocontrol of sugarcane wilt and red rot fungi, increases in the number of tillers, plant height, and girth of cane inoculated with the consortium of *B. lentimorbus* NRRL B-30486, *B. subtilis* NRRL B-30487, and *B. lentimorbus* NRRL B-30488 using vermiculite as carrier, compared with un-inoculated control.

EXAMPLE 18

Field Trial of Plant Growth Promotion Activity of the Consortium of *B. lentimorbus* NRRL B-30486, *B. subtilis* NRRL B-30487, and *B. lentimorbus* NRRL B-30488 Using Vermiculite as Carrier, on Sugarcane at Rozagaon Field trials using sugarcane were conducted by placing sugarcane sets at the time of sowing directly on vermiculite containing the consortium of *B. lentimorbus* NRRL B-30486, *B. subtilis* NRRL B-30487, and *B. lentimorbus* NRRL B-30488, prepared as described in Example 8. The sugarcane trial was set up in October 2000 at Dhampur Sugar Mills Ltd., Rozagaon. After nine months of plant growth the number of tillers, plant height, girth, millable cane, and cane yield of sugarcane were noted in December 2001. For the field trials sugarcane variety Cos-95255 was used at Dhampur Sugar Mills Ltd., Rozagaon. The test results of the field trials of plant growth promotion activity of the consortium of *B. lentimorbus* NRRL B-30486, *B. subtilis* NRRL B-30487, and *B. lentimorbus* NRRL B-30488 using vermiculite as carrier, on sugarcane are given in Table 15.

TABLE 15

| | Treatment | | |
|---|---|---|---|
| Observations | Un-inoculated control | Inoculated | % increase over control |
| Number of tillers/plant | 6.2 | 11.0 | 77.42 |
| Plant height (cm) | 200 | 246 | 23.0 |
| Girth of cane (cm) | 9.1 | 11.24 | 23.52 |
| Millable cane | 5 | 8 | 60.0 |
| Cane yield/plot (kg) | 128 | 229 | 78.9 |

The results presented in Table 15 clearly show increases in the number of tillers, plant height, girth, millable cane, and cane yield of cane inoculated with the consortium of *B. lentimorbus* NRRL B-30486, *B. subtilis* NRRL B-30487, and *B. lentimorbus* NRRL B-30488 using vermiculite as carrier, compared with un-inoculated control.

EXAMPLE 19

Field Trial of Plant Growth Promotion Activity of the Consortium of *B. lentimorbus* NRRL B-30486, *B. subtilis* NRRL B-30487, and *B. lentimorbus* NRRL B-30488 Using Vermiculite as Carrier, on Sugarcane at Dhampur Field trials using sugarcane were conducted by placing sugarcane sets at the time of sowing directly on vermiculite containing the consortium of *B. lentimorbus* NRRL B-30486, *B. subtilis* NRRL B-30487, and *B. lentimorbus* NRRL B-30488, prepared as described in Example 8. Sugarcane trials were set up in November, 2000 at Dhampur Sugar Mills Ltd., Dhampur, Bijnour. After thirteen months of plant growth, the number of tillers, plant height, and girth of sugarcane were noted in December, 2001. For the field trials sugarcane variety Cos-95255 was used. The test results of the field trials of plant growth promotion activity of the consortium of *B. lentimorbus* NRRL B-30486, *B. subtilis* NRRL B-30487, and *B. lentimorbus* NRRL B-30488 using vermiculite as carrier, on sugarcane are given in Table 16.

TABLE 16

| | Treatment | | |
|---|---|---|---|
| Observations | Un-inoculated control | Inoculated | % increase over control |
| Number of tillers/plant | 6.0 | 8.4 | 40.0 |
| Plant height (cm) | 220 | 251 | 14.09 |
| Girth of cane (cm) | 7.2 | 9.4 | 30.56 |
| Millable cane | 4 | 9 | 125.0 |
| Cane yield/plot (kg) | 128 | 217 | 69.53 |

The results presented in Table 16 show increases in the number of tillers, plant height, girth of cane, millable cane, and cane yield inoculated with the consortium of *B. lentimorbus* NRRL B-30486, *B. subtilis* NRRL B-30487, and *B. lentimorbus* NRRL B-30488 using vermiculite as carrier, compared with un-inoculated control.

EXAMPLE 20

Field Trial of Plant Growth Promotion Activity of the Consortium of *B. lentimorbus* NRRL B-30486, *B. subtilis* NRRL B-30487, and *B. lentimorbus* NRRL B-30488 Using Charcoal as Carrier, on Sugarcane Field trials using sugarcane were conducted by placing sugarcane sets at the time of sowing directly on vermiculite containing the consortium of *B. lentimorbus* NRRL B-30486, *B. subtilis* NRRL B-30487, and *B. lentimorbus* NRRL B-30488, prepared as described in Example 13. A sugarcane trial was set up in April, 2001 at Dhampur Sugar Mills Ltd., Dhampur. After ten months of plant growth, the number of tillers, plant height, girth, millable cane, and cane yield of sugarcane were noted in December, 2001. For the field trials sugarcane variety Cos-89003 was used at Dhampur Sugar Mills Ltd., Dhampur. The test results of the field trials of plant growth promotion activity of the consortium of *B. lentimorbus* NRRL B-30486, *B. subtilis* NRRL B-30487, and *B. lentimorbus* NRRL B-30488 using charcoal as carrier, on sugarcane are given in Table 17.

TABLE 17

| | Treatment | | |
|---|---|---|---|
| Observations | Un-inoculated control | Inoculated | % increase over control |
| Number of tillers/plant | 7.2 | 10.8 | 50.0 |
| Plant height (cm) | 255 | 289 | 13.33 |
| Girth of cane (cm) | 9.2 | 10.8 | 17.33 |
| Millable cane | 5 | 9 | 80.0 |
| Cane yield/plot (kg) | 162 | 208 | 28.39 |

The results presented in Table 17 show increases in the number of tillers, plant height, and girth of cane, millable cane, and cane yield inoculated with the consortium of *B. lentimorbus* NRRL B-30486, *B. subtilis* NRRL B-30487, and *B. lentimorbus* NRRL B-30488 using charcoal as carrier, compared with un-inoculated control.

EXAMPLE 21

Field Trial of Plant Growth Promotion Activity of the Consortium of *B. lentimorbus* NRRL B-30486, *B. subtilis*

NRRL B-30487, and *B. lentimorbus* NRRL B-30488 Using Fermented Sugar Factory Sulphitation Press Mud and Distillery Spent Wash as Carrier, on Sugarcane at Dhampur Field trials using sugarcane were conducted by placing sugarcane sets at the time of sowing directly on fermented sugar factory sulphitation press mud and distillery spent wash as carrier containing the consortium of *B. lentimorbus* NRRL B-30486, *B. subtilis* NRRL B-30487, and *B. lentimorbus* NRRL B-30488, prepared as described in Example 14. A sugarcane trial was set up in May, 2001 at Dhampur Sugar Mills Ltd., Dhampur. After ten months of plant growth the number of tillers, plant height, girth of sugarcane, millable cane, and cane yield were noted in December, 2001. For the field trials sugarcane variety Cos-89003 was used at Dhampur Sugar Mills Ltd., Dhampur. The test results of the field trials of plant growth promotion activity of the consortium of *B. lentimorbus* NRRL B-30486, *B. subtilis* NRRL B-30487, and *B. lentimorbus* NRRL B-30488 using fermented sugar factory sulphitation press mud and distillery spent wash as carrier, on sugarcane are given in Table 18.

TABLE 18

| Observations | Treatment<br>Un-inoculated control | Inoculated | % increase over control |
|---|---|---|---|
| Number of tillers/plant | 6.2 | 14 | 125.8 |
| Plant height (cm) | 248 | 285 | 14.91 |
| Girth of cane (cm) | 6.4 | 11.2 | 75.0 |
| Millable cane | 6 | 11 | 83.33 |
| Cane yield/plot (kg) | 164 | 237 | 44.51 |

The results presented in Table 18 show increases in the number of tillers, plant height, girth of cane, millable cane, and cane yield inoculated with the consortium of *B. lentimorbus* NRRL B-30486, *B. subtilis* NRRL B-30487, and *B. lentimorbus* NRRL B-30488 using fermented sugar factory sulphitation press mud and distillery spent wash as carrier, compared with un-inoculated control.

EXAMPLE 22

Field Trial of Plant Growth Promotion Activity of the Consortium of *B. lentimorbus* NRRL B-30486, *B. subtilis* NRRL B-30487, and *B. lentimorbus* NRRL B-30488 Using Fermented Sugar Factory Sulphitation Press Mud as Carrier, on Sugarcane at Dhampur Field trials using sugarcane were conducted by placing sugarcane sets at the time of sowing directly on fermented sugar factory sulphitation press mud and distillery spent wash as carrier containing the consortium of *B. lentimorbus* NRRL B-30486, *B. subtilis* NRRL B-30487, and *B. lentimorbus* NRRL B-30488, prepared as described in Example 14. A sugarcane trial was set up in May, 2001 at Dhampur Sugar Mills Ltd., Dhampur. After ten months of plant growth the number of tillers, plant height, girth of sugarcane, millable cane, and cane yield were noted in December, 2001. For the field trials sugarcane variety Cos-89003 was used at Dhampur Sugar Mills Ltd., Dhampur. The test results of the field trials of plant growth promotion activity of the consortium of *B. lentimorbus* NRRL B-30486, *B. subtilis* NRRL B-30487, and *B. lentimorbus* NRRL B-30488 using fermented sugar factory sulphitation press mud as carrier, on sugarcane are given in Table 19.

TABLE 19

| Observations | Treatment<br>Un-inoculated control | Inoculated | % increase over control |
|---|---|---|---|
| Number of tillers/plant | 6.2 | 16 | 158.0 |
| Plant height (cm) | 248 | 313 | 26.2 |
| Girth of cane (cm) | 6.4 | 12.0 | 87.5 |
| Millable cane | 6 | 11.8 | 96.6 |
| Cane yield/plot (kg) | 164 | 256 | 56.0 |

The results presented in Table 19 show increases in the number of tillers, plant height, girth of cane, millable cane, and cane yield when inoculated with the consortium of *B. lentimorbus* NRRL B-30486, *B. subtilis* NRRL B-30487, and *B. lentimorbus* NRRL B-30488 using fermented sugar factory sulphitation press mud as carrier, compared with un-inoculated control.

EXAMPLE 23

Field Trial of Plant Growth Promotion Activity of the Consortium of *B. lentimorbus* NRRL B-30486, *B. subtilis* NRRL B-30487, and *B. lentimorbus* NRRL B-30488 Using Fermented Sugar Factory Carbonation Press Mud as Carrier, on Sugarcane at Rozagaon Field trials using sugarcane were conducted by placing sugarcane sets at the time of sowing directly on fermented sugar factory carbonation press mud as carrier containing the consortium of *B. lentimorbus* NRRL B-30486, *B. subtilis* NRRL B-30487, and *B. lentimorbus* NRRL B-30488, prepared as described in Example 15. A sugarcane trial was set up in May, 2001 at Dhampur Sugar Mills Ltd., Rozagaon. After eight months of plant growth the number of tillers, plant height, girth of sugarcane, millable cane, and cane yield were noted in December, 2001. For the field trials sugarcane variety Cos-96258 was used at Dhampur Sugar Mills Ltd., Rozagaon. The test results of the field trials of plant growth promotion activity of the consortium of *B. lentimorbus* NRRL B-30486, *B. subtilis* NRRL B-30487, and *B. lentimorbus* NRRL B-30488 using fermented sugar factory carbonation press mud as carrier, on sugarcane are given in Table 20.

TABLE 20

| Observations | Treatment<br>Un-inoculated control | Inoculated | % increase over control |
|---|---|---|---|
| Number of tillers/plant | 6 | 13 | 116.6 |
| Plant height (cm) | 230 | 265 | 15.22 |
| Girth of cane (cm) | 7.2 | 9.5 | 31.94 |
| Millable cane | 5 | 11 | 120.0 |
| Cane yield/plot (kg) | 182 | 280 | 53.85 |

The results presented in Table 20 show increases in the number of tillers, plant height, girth of cane, millable cane, and cane yield when inoculated with the consortium of *B. lentimorbus* NRRL B-30486, *B. subtilis* NRRL B-30487, and *B. lentimorbus* NRRL B-30488 using fermented sugar factory carbonation press mud as carrier, compared with un-inoculated control.

EXAMPLE 24

Comparative Analysis of Effect of Pesticides on the Growth of B. lentimorbus NRRL B-30486, B. subtilis NRRL B-30487, and B. lentimorbus NRRL B-30488

The three bacterial strains B. lentimorbus NRRL B-30486, B. subtilis NRRL B-30487, and B. lentimorbus NRRL B-30488 were screened to evaluate the effect of pesticides on its growth as follows: Evaluation of the effect of pesticides on the growth of the bacterial strains in broth was carried out using Erlenmeyer flasks (150 ml) containing 40 ml of medium inoculated in triplicate with the bacterial strain (100 μl inoculum with approximately $10^6$ cfu/ml). Value refers to the number of cells (Log cfu/ml) of strains when individually grown for 1 day in NB, at 30° C. in the presence of pesticide, as per recommended dose of its application. The effect of pesticide on its growth has been presented in Table 20. Inoculated batch cultures, without any pesticides, served as control. Flasks were incubated for 1 day at 30° C. on a New Brunswick Scientific, USA, Innova Model 4230 refrigerated incubator shaker at 180 rpm.

TABLE 21

| Pesticide | | Log cfu/ml | | |
|---|---|---|---|---|
| (Active ingredient) | Recommended dose | B-30486 | B-30487 | B-30488 |
| Control | 0 | 7 | 9 | 7 |
| FUNGICIDES | | | | |
| Mancozeb 75% WP* | 3 g/L | 2 | 2 | NG** |
| Copper oxychloride 50% WP | 6 g/L | 5 | 2 | 3 |
| Chlorothalonil 75% WP | 3 g/L | NG | 2 | NG |
| Tridemorph 80% EC*** | 2 ml/L | 5 | 6 | NG |
| Triadimefon 25% WP | 4 g/L | 5 | 6 | 5 |
| Carbendazim 50% WP | 4 g/L | 8 | 10 | 10 |
| Carboxin 75% WP | 4 g/L | 5 | 3 | NG |
| Metalaxyl 8% + Mancozeb 64% WP | 2 g/L | 10 | 10 | 10 |
| Thiophanate-Methyl 70% WP | 3 g/L | 5 | 9 | 8 |
| INSECTICIDES | | | | |
| Monocrotophos 36% SL**** | 1 ml/L | 3 | 10 | 5 |
| Dimethoate 30% EC | 2 ml/L | 4 | 7 | 5 |
| Oxydemeton-methyl 25% EC | 2 ml/L | 7 | 9 | 7 |
| Deltamethrin 2.8% EC | 2 ml/L | 10 | 10 | 10 |
| Endosulfan 35% EC | 2 ml/L | 6 | 7 | 5 |
| Dicofol 18.5% EC | 2.7 ml/L | NG | 5 | 3 |
| Chlorpyriphos 20% EC | 2.5 ml/L | 3 | 5 | 3 |

*WP = Wettable powder;
**NG = No growth;
***EC = Emulsifying concentrate;
****SL = Soluble liquid The results presented in Table 21 demonstrate variable effect of pesticides on the growth of B. lentimorbus NRRL B-30486, B. subtilis NRRL B-30487, and B. lentimorbus NRRL B-30488. Among various pesticides tested, carbendazim 50% W.P., metalaxyl 8%+mancozeb 64% W.P., and deltamethrin 2.8% E.C. were most compatible for application with B. lentimorbus NRRL B-30486, B. subtilis NRRL B-30487, and B. lentimorbus NRRL B-30488.

It is understood that the foregoing detailed description is given merely by way of illustration and that modification and variations may be made therein without departing from the spirit and scope of the invention.

The invention claimed is:

1. A bioinoculant composition comprising cells of at least one purified culture of a Bacillus species selected from the group consisting of
   i) a Bacillus lentimorbus deposited as NRRL B-30486 exhibiting the following characteristics: a rod shape 1.5 to 2.0 microns in width and 3.0 to 6.0 microns in length, gram positive, negative catalase reaction, positive for anaerobic growth, negative Voges-Proskauer reaction, pH in V-P broth of 5.5, produces acid from D-glucose but not from L-arabinose, D-xylose or D-mannitol, produces gas from glucose, negative for hydrolysis of casein, gelatin and starch, negative for use of citrate, negative for conversion of nitrate to nitrite, negative for indole formation, grows on nutrient broth at pH 5.7 and at pH 6.8, grows in medium containing sodium chloride up to 10%, grows at a temperature of up to 55° C.;
   ii) a Bacillus subtilis deposited as NRRL B-30487 exhibiting the following characteristics: an oval shape 2.5 microns in width, gram positive, positive catalase reaction, negative for anaerobic growth, positive Voges-Proskauer reaction, pH in V-P broth of 5.8, produces acid from D-glucose, L-arabinose, D-xylose and D-mannitol, does not produce gas from glucose, positive for hydrolysis of casein, gelatin and starch, positive for use of citrate, positive for conversion of nitrate to nitrite, negative for indole formation, grows on nutrient broth at pH 5.7 and at pH 6.8, grows in medium containing sodium chloride up to 5%, grows at a temperature of up to 55° C.; and
   iii) a Bacillus lentimorbus deposited as NRRL B-30488 exhibiting the following characteristics: a rod shape 1.5 to 2.0 microns in width and 5.0 to 10.0 microns in length, gram positive, negative catalase reaction, positive for anaerobic growth, negative Voges-Proskauer reaction, pH in V-P broth of 5.2, produces acid from D-glucose but not from L-arabinose, D-xylose or D-mannitol, produces gas from glucose, negative for hydrolysis of casein, gelatin and starch, negative for use of citrate, negative for conversion of nitrate to nitrite, negative for indole formation, grows on nutrient broth at pH 5.7 and at pH 6.8, grows in medium containing sodium chloride up to 10%, grows at a temperature of up to 55° C.;
and optionally a carrier.

2. The bioinoculant composition of claim 1, that comprises at least two of the strains i), ii) and iii).

3. The bioinoculant composition of claim 1, that comprises all three of the strains i), ii) and iii).

4. The bioinoculant composition of claim 3, in which the three strains are present in approximately equal amounts.

5. The bioinoculant composition of claim 1, in which the concentration of the cells of each strain is from $10^4$ to $10^{10}$ cfu/g of carrier.

6. The bioinoculant composition of claim 1, in which the concentration of the cells of each strain is from $10^7$ to $10^8$ cfu/g of carrier.

7. The bioinoculant composition of claim 1, in which the total concentration of the cells is from $10^4$ to $10^{10}$ cfu/g of carrier.

8. The bioinoculant composition of claim 1, in which the total concentration of the cells is from $10^7$ to $10^8$ cfu/g of carrier.

9. The bioinoculant composition of claim 1, in which the generation time of the cells is 55 to 65 minutes when cultured at 30° C.

10. The bioinoculant composition of claim 1, in which the cells colonize the roots of a plant that contact the composition.

11. The bioinoculant composition of claim 1, in which the carrier is present and comprises a gum or a sugar.

12. The bioinoculant composition of claim 1, in which the carrier is present and comprises VERMICULITE, charcoal, carbonation press mud from sugar refining, or a mixture of sulphitation press mud from sugar refining and distillery spent wash.

13. A method for promoting the growth of a plant comprising applying the bioinoculant of claim 1 to a seed of the plant, to soil in which the plant is growing or to the plant directly.

14. The method of claim 13, in which the bioinoculant is applied to soil to provide $10^6$ to $10^8$ cfu/g of soil.

15. The method of claim 13, in which the bioinoculant composition is applied to seed to provide $10^7$ to $10^9$ cfu/seed.

* * * * *